US011536713B2

(12) United States Patent
Suzuki et al.

(10) Patent No.: US 11,536,713 B2
(45) Date of Patent: Dec. 27, 2022

(54) METHOD FOR SEARCHING AND SCREENING FOR TARGET OF ANTI-CANCER AGENT USING NON-HUMAN ANIMAL MODEL HAVING NOG ESTABLISHED CANCER CELL LINE TRANSPLANTED THEREIN

(75) Inventors: Masami Suzuki, Shizuoka (JP); Koichi Matsubara, Helios (SG); Atsuhiko Kato, Shizuoka (JP); Chie Kato, Shizuoka (JP); Shinta Kobayashi, Helios (SG); Yu Jau Chen, Helios (SG); Masaki Yamazaki, Helios (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/519,059

(22) PCT Filed: Dec. 24, 2010

(86) PCT No.: PCT/JP2010/073266
§ 371 (c)(1),
(2), (4) Date: Oct. 5, 2012

(87) PCT Pub. No.: WO2011/078301
PCT Pub. Date: Jun. 30, 2011

(65) Prior Publication Data
US 2013/0019327 A1 Jan. 17, 2013

(30) Foreign Application Priority Data
Dec. 25, 2009 (JP) .............................. JP2009-295426

(51) Int. Cl.
*G01N 33/50* (2006.01)
*A01K 67/027* (2006.01)
(52) U.S. Cl.
CPC ...... *G01N 33/5011* (2013.01); *A01K 67/0271* (2013.01); *G01N 33/5088* (2013.01); *A01K 2207/12* (2013.01); *A01K 2227/105* (2013.01); *A01K 2267/0331* (2013.01)
(58) Field of Classification Search
CPC ....... A01K 2267/0331; A01K 2207/12; G01N 33/5011; C12Q 1/6886
See application file for complete search history.

(56) References Cited

U.S. PATENT DOCUMENTS

| 5,573,924 | A | 11/1996 | Beckmann et al. |
| 7,145,055 | B2* | 12/2006 | Ito et al. ............. 800/3 |
| 2002/0119565 | A1* | 8/2002 | Clarke et al. ........ 435/366 |
| 2007/0220621 | A1 | 9/2007 | Clarke et al. |
| 2008/0064049 | A1 | 3/2008 | Clarke et al. |
| 2008/0178305 | A1 | 7/2008 | Clark et al. |
| 2008/0268476 | A1 | 10/2008 | Lopez |
| 2009/0081221 | A1 | 3/2009 | Tokoro et al. |
| 2009/0148942 | A1 | 6/2009 | McDonagh et al. |
| 2009/0214517 | A1 | 8/2009 | Wong et al. |
| 2009/0226396 | A1* | 9/2009 | Haley ................ G01N 33/5011 424/85.2 |
| 2009/0324491 | A1 | 12/2009 | Aburatani et al. |
| 2010/0003265 | A1 | 1/2010 | Scheffler et al. |
| 2010/0024049 | A1 | 1/2010 | Marchiano |
| 2010/0275280 | A1 | 10/2010 | Clevers et al. |
| 2010/0287638 | A1 | 11/2010 | Dirks et al. |
| 2011/0182904 | A1 | 7/2011 | Zimmerman et al. |
| 2011/0244502 | A1 | 10/2011 | Ince et al. |
| 2013/0288248 | A1 | 10/2013 | Yamazaki et al. |
| 2014/0302511 | A1 | 10/2014 | Yamazaki et al. |
| 2014/0314675 | A1 | 10/2014 | Yamazaki et al. |
| 2016/0017028 | A1 | 1/2016 | Yoshida et al. |
| 2016/0159904 | A1 | 6/2016 | Yamazaki et al. |

(Continued)

FOREIGN PATENT DOCUMENTS

| CA | 2 447 400 | 3/2005 |
| CN | 101014608 A | 8/2007 |
| CN | 101506352 | 8/2009 |

(Continued)

OTHER PUBLICATIONS

Dewan Zahidunnabi et al., Potential role of NK cells in tumor growth and metastasis of breast cancer cells in NOD/SCID/ cnull (NOG) mice: Implication of immune therapy. Proc Amer Assoc Cancer Res, vol. 46, 2005, Abstract #4683, p. 1.*

(Continued)

Primary Examiner — Scott Long
(74) Attorney, Agent, or Firm — Klarquist Sparkman, LLP

(57) ABSTRACT

An objective of the present invention is to provide non-human animal models of cancer pathology, which mimic the hierarchical organization, cancer progression process, or biological property of human cancer tissues, and uses thereof. To achieve the objective described above, first, the present inventors transplanted cells of NOG-established cancer lines into NOG mice and morphologically observed the resulting tissue organization. As a result, the non-human animal models were demonstrated to exhibit pathologies (the hierarchical organization, cancer progression process, or biological properties of the cancer cells) similar to that of human cancer. Specifically, the present inventors succeeded in preparing non-human animal models exhibiting pathologies more similar to a human cancer, and cell culture systems using NOG-established cancer cell lines where the in vitro cell morphology is more similar to that of human cancer.

6 Claims, 13 Drawing Sheets

(56) References Cited

U.S. PATENT DOCUMENTS

2020/0325222 A1  10/2020  Yamazaki et al.
2020/0385686 A1  12/2020  Yamazaki et al.

FOREIGN PATENT DOCUMENTS

| | | |
|---|---|---|
| EP | 1 338 198 A1 | 8/2003 |
| EP | 1 637 589 A1 | 3/2006 |
| EP | 1 686 173 A1 | 8/2006 |
| EP | 1 792 979 | 6/2007 |
| EP | 1815864 | 8/2007 |
| EP | 2070548 | 6/2009 |
| EP | 2517555 | 10/2012 |
| EP | 2626414 | 8/2013 |
| JP | 2005-206508 | 8/2005 |
| JP | 3753321 | 12/2005 |
| JP | 2007-530588 | 11/2007 |
| JP | 2008-500838 | 1/2008 |
| JP | 2008-102012 | 5/2008 |
| JP | 2008-514205 | 5/2008 |
| JP | 2008-182912 | 8/2008 |
| JP | 2009-502156 | 1/2009 |
| JP | 2009-509510 | 3/2009 |
| JP | 2009/519242 | 5/2009 |
| JP | 2009-539374 | 11/2009 |
| JP | 2010-516259 | 5/2010 |
| JP | 2011-519567 | 7/2011 |
| WO | WO 02/12447 | 2/2002 |
| WO | WO 03/104401 | 12/2003 |
| WO | WO 2004/101775 A1 | 11/2004 |
| WO | WO 2005/035740 A1 | 4/2005 |
| WO | WO 2005/092927 | 10/2005 |
| WO | WO 2005/118824 | 12/2005 |
| WO | WO 2005/118824 A2 | 12/2005 |
| WO | WO 2006/039671 | 4/2006 |
| WO | WO 2006/039678 A2 | 4/2006 |
| WO | WO 2006/051405 | 5/2006 |
| WO | WO 2006/051984 A1 | 5/2006 |
| WO | WO 2006/138275 | 12/2006 |
| WO | WO 2007/012811 | 2/2007 |
| WO | WO 2007/038637 | 4/2007 |
| WO | WO 2007/064945 | 6/2007 |
| WO | WO 2007/064945 A2 | 6/2007 |
| WO | WO 2007/132883 A1 | 11/2007 |
| WO | WO 2007/145901 | 12/2007 |
| WO | WO 2008/017171 | 2/2008 |
| WO | WO 2008/047723 | 4/2008 |
| WO | WO 2008/091908 | 7/2008 |
| WO | WO 2008/143954 | 11/2008 |
| WO | WO 2008/149803 | 12/2008 |
| WO | WO 2009/005809 | 1/2009 |
| WO | WO 2009/064301 | 5/2009 |
| WO | WO 2009/135181 | 11/2009 |
| WO | WO 2010/009121 | 1/2010 |
| WO | WO 2010/016766 | 2/2010 |
| WO | WO 2010/067487 | 6/2010 |
| WO | WO 2010/102244 | 9/2010 |
| WO | WO 2010/113117 | 10/2010 |
| WO | WO 2010/123891 | 10/2010 |
| WO | WO 2010/126074 | 11/2010 |
| WO | WO 2011/027308 | 3/2011 |
| WO | WO 2011/083088 | 7/2011 |
| WO | WO 2012/046797 | 4/2012 |
| WO | WO 2013/035824 | 3/2013 |
| WO | WO 2013/062083 | 5/2013 |

OTHER PUBLICATIONS

Imada et al., Serial Transplantation of Adult T Cell Leukemia Cells into Severe Combined Immunodeficient Mice. Jpn. J. Cancer Res. 87, 887-892, Sep. 1996.*

Morisot et al., Leukemia Stem Cells (LSCs) Are Frequent in Childhood Precursor B Acute Lymphoblastic Leukemia (ALL). 50$^{th}$ ASH Annual Meeting and Exposition. Dec. 6, 2008, p. 1-2.*

Mani et al., The epithelial-mesenchymal transition generates cells with properties of stem cells. Cell. May 16, 2008; 133(4): 704-715.*

Suemizu et al., Identification of a key molecular regulator of liver metastasis in human pancreatic carcinoma using a novel quantitative model of metastasis in NOD/SCID/gammac null (NOG) mice. International Journal of Oncology 31: 741-751, 2007.*

Oka et al., Immunohistochemical evaluation of E-cadherin adhesion molecule expression in human gastric cancer. Virchows Archiv A Pathol Anat (1992) 421: 149-156.*

Chen et al., Intestinal Adenomagenesis Involves Core Molecular Signatures of the Epithelial-Mesenchymal Transition. J Mol Histol. Jun. 2008 ; 39(3): 283-294.*

Petrova et al., Transcription Factor PROX1 Induces Colon Cancer Progression by Promoting the Transition from Benign to Highly Dysplastic Phenotype. Cancer Cell 13, 407-419, May 2008 (Year: 2008).*

Sun et al., An ultra-metastatic model of human colon cancer in nude mice (Clin Exp Metastasis, 1999, 17:41-48) (Year: 1999).*

Corbett et al., Tumor Induction Relationships in Development of Transplantable Cancers of the Colon in Mice for Chemotherapy Assays, with a Note on Carcinogen Structure. Cancer Res., 1975, 35:2434-2439 (Year: 1975).*

Sanz et al., Differential transplantability of human endothelial cells in colorectal cancer and renal cell carcinoma primary xenografts. Laboratory Investigation (2009) 89, 91-97 (Year: 2009).*

U.S. Appl. No. 13/878,181, filed Jul. 5, 2013, Yamazaki et al.

Fang et al., "Expansion of CD133$^{+}$ colon cancer cultures retaining stem cell properties to enable cancer stem cell target discovery," *British Journal of Cancer*, vol. 102, pp. 1265-1275, 2010.

Inagaki et al. "Long-term maintenance of brain tumor stem cell properties under at non-adherent and adherent culture conditions," *Biochem. Biophys. Res. Commun.*, vol. 361, No. 3, pp. 586-592, 2007.

Ishizawa et al., "Tumor-Initiating Cells are Rare in Many Human Tumors," *Cell Stem Cell*, vol. 7, pp. 279-282, 2010.

O'Brien et al., "A human colon cancer cell capable of initiating tumour growth immunodeficient mice," *Nature*, vol. 445, pp. 106-110, 2007.

Quintana et al., "Efficient tumour formation by single human melanoma cells," *Nature*, vol. 456, pp. 593-598, 2008.

Vermeulen et al, "Single-cell cloning of colon cancer stem cells reveals a multi-lineage differentiation capacity," *Proc. Natl. Acad. Sci. USA*, vol. 105, No. 36, pp. 13427-134132, 2008.

Vermeulen et al., "Wnt activity defines colon cancer stem cells and is regulated by the microenvironment," *Nature Cell Biology*, vol. 12, No. 5, pp. 468-476, 2010.

Yeung et al., "Cancer stem cells from colorectal cancer-derived cell lines," *Proc. Natl. Acad. Sci. USA*, vol. 107, No. 8, pp. 3722-3727, 2010.

Machida et al., "Higher susceptibility of NOG mice to xenotransplanted tumors," *J. Toxicol. Sci.* vol. 34, No. 1, pp. 123-127, 2009.

Hu and Smyth, ELDA; Extreme Limiting Dilution analysis for comparing depleted and enriched populations in stem cell and other assays. Journal of Immunological Methods, 2009. 347, 70-78.

Office action dated Jul. 22, 2014 for U.S. Appl. No. 13/878,181 (27 pages).

Gou et al., "Establishment of Clonal Colony-Forming Assay for Propagation of Pancreatic Cancer Cells With Stem Cell Properties," *Pancreas*, vol. 34, No. 4, pp. 429-435, 2007.

Hermann et al., "Distinct Populations of Cancer Stem Cells Determine Tumor Growth and Metastatic Activity in Human Pancreatic Cancer," *Cell Stem Cell*, vol. 1, pp. 313-323, 2007.

Ku et al., "Establishment and characterization of 13 human colorectal carcinoma cell lines: mutations of genes and expressions of drug-sensitivity genes and cancer stem cell markers," *Carcinogenesis* vol. 31, No. 6, pp. 1003-1009, 2010.

Vermeulen et al., "Single-cell cloning of colon cancer stem cells reveals a multi-lineage differentiation capacity," *PNAS* vol. 105, No. 36, pp. 13427-13432, 2008.

Office Action (Restriction Requirement) dated Feb. 25, 2014 for U.S. Appl. No. 13/878,181 (10 pages).

(56) References Cited

OTHER PUBLICATIONS

Amendment and Response to Restriction Requirement for U.S. Appl. No. 13/878,181, submitted to PTO on May 23, 2014 (12 pages).
International Preliminary Report on Patentability from PCT Application No. PCT/JP2012/072852 (in English), dated Mar. 12, 2014 (11 pages).
Amendment and Response to Non-Final Office Action, submitted Jan. 22, 2015, in connection with U.S. Appl. No. 13/878,181, in response to the Non-Final Office Action dated Jul. 22, 2014.
European Search Report, dated Aug. 27, 2014, for EPC Patent Application No. 10839531.0 (5 pages).
Fujii et al., "The Potential of the NOD/SCID/$\gamma_c^{null}$ (NOG) Mouse as an In Vivo Human Tissue Model," Toxicol. Pathol., vol. 35, p. 191-P53, 2007 (1 page).
Fujii et al., "The Potential of the NOD/SCID/$\gamma_c^{null}$ (NOG) Mouse as an In Vivo Human Tissue Model," The 25th Annual Meeting of the Society of Toxicologic Pathology, Vancouver, Canada; Jun. 18-22, 2006 (2 pages).
Kobayash1 et al., "LGR5-Positive Colon Cancer Stem Cells Interconvert with Drug-Resistant LGR5-Negative Cells and Are Capable of Tumor Reconstitution," Stem Cells, vol. 30, No. 12, pp. 2631-2644, 2012.
Carlone and Breault, "Slowly cycling versus rapidly cycling intestinal stem cells," Cell Cycle 10(5):723-724, 2011.
English translation of the International Search Report for PCT/JP2012/072852, dated Nov. 27, 2012.
International Preliminary Report on Patentability (English language translation) for PCT Application No. PCT/JP2012/077714, 13 pages (dated Apr. 29, 2014).
International Search Report on Patentability from PCT/JP2010/073266 (2 pages) (dated Mar. 28, 2011).
Kobayashi et al., "LGR5-Positive Colon Cancer Stem Cells Interconvert with Drug-Resistant LGR5-Negative Cells and are Capable of Tumor Reconstitution," Stem Cells, vol. 30:2631-2644, 2012.
Machine English translation of PCT Publication No. WO 2010/126074, Matsumoto et al., published Nov. 4, 2010.
Munoz et al., "The Lgr5 Intestinal Stem Cell Signature: Robust Expression of Proposed Quiescent '+ 4' Cell Markers," EMBO J., vol. 31:3079-3091, 2012.
Translation of the International Preliminary Report on Patentability, International Application No. PCT/JP2011/073067, May 16, 2013.
Walker et al., "LGR5 is a Negative Regulator of Tumourigenicity, Antagonizes Wnt Signalling and Regulates Cell Adhesion in Colorectal Cancer Cell Lines," PLoS ONE, vol. 6:e22733, 2011.
U.S. Appl. No. 14/343,364, filed Mar. 6, 2014, Yamazaki, et al.
U.S. Appl. No. 14/354,517, filed Apr. 25, 2014, Yamazaki, et al.
Al-Hajj, et al. "Prospective identification of tumorigenic breast cancer cells." Proceedings of the National Academy of Sciences 100:3983-3988, 2003.
Barker, et al. "Crypt stem cells as the cells-of-origin of intestinal cancer." Nature 457: 608-611, 2009.
Barker, et al. "Identification of stem cells in small intestine and colon by marker gene Lgr5." Nature 449: 1003-1007, 2007.
Boiko, et al. "Human melanoma-initiating cells express neural crest nerve growth factor receptor CD271." Nature 466.7302 (2010: 133-137, 2010.
Bonnet et al. "Human acute myeloid leukemia is organized as a hierarchy that originates from a primitive hematopoietic cell." Nature Medicine 3: 730-737, 1997.
Chu, et al. "Characterization of a subpopulation of colon cancer cells with stem cell-like properties." International Journal of Cancer 124: 1312-1321, 2009.
Clevers. "The cancer stem cell: premises, promises and challenges." Nature Medicine 17:313-319, 2011.
Collins, et al. "Prospective identification of tumorigenic prostate cancer stem cells." Cancer Research 65: 10946-10951, 2005.
Dalerba, et al. "Phenotypic characterization of human colorectal cancer stem cells." Proceedings of the National Academy of Sciences 104: 10158-10163., 2007.

Eramo, et al. "Identification and expansion of the tumorigenic lung cancer stem cell population." Cell Death & Differentiation 15: 504-514, 2007.
Haraguchi, et al. "CD 133+ CD44+ population efficiently enriches colon cancer initiating cells." Annals of Surgical Oncology 152927-2933, 2008.
Hermann, et al. "Distinct populations of cancer stem cells determine tumor growth and metastatic activity in human pancreatic cancer." Cell Stem Cell 1:313-323, 2007.
Hsu, et al. "Characterization of Two LGR Genes Homologous to Gonadotropin and Thyrotropin Receptors with Extracellular Leucine-Rich Repeats and a G Protein-Coupled, Seven-Transmembrane Region." Molecular Endocrinology 12: 1830-1845, 1998.
Huang, et al. "ALDH1 is a marker for normal and malignant human colonic stem cells and tracks stem cell overpopulation during colon tumorigenesis." Cancer Res 69:3382-3389, 2009.
International Search Report for PCT/JP2012/077714, mailed by the ISA (Japanese Patent Office) dated Jan. 29, 2013 (5 pages).
Ishizawa, et al. "Tumor-initiating cells are rare in many human tumors." Cell Stem Cell 7:279-282, 2010.
Kowalczyk, et al. "Molecular and therapeutic characterization of anti-ectodysplasin A receptor (EDAR) agonist monoclonal antibodies." Journal of Biological Chemistry 286: 30769-30779, 2011.
Lapidot, et al. "A cell initiating human acute myeloid leukaemia after transplantation into SCID mice." Nature 367: 645-648, 1994.
Li, et al. "Identification of pancreatic cancer stem cells." Cancer Research 67: 1030-1037, 2007.
McDonald, et al. "Identification and cloning of an orphan G protein-coupled receptor of the glycoprotein hormone receptor subfamily." Biochemical and Biophysical Research Communications 247: 266-270, 1998.
O'Brien, et al. "A human colon cancer cell capable of initiating tumour growth in immunodeficient mice." Nature 445: 106-110, 2007.
Pang, et al. "A Subpopulation of CD26+ Cancer Stem Cells with Metastatic Capacity in Human Colorectal Cancer." Cell Stem Cell 6: 603-615, 2010.
Park, et al. "Cancer stem cell-directed therapies: recent data from the laboratory and clinic." Molecular Therapy 17: 219-230, 2009.
Patrawala, et al. "Highly purified CD44+ prostate cancer cells from xenograft human tumors are enriched in tumorigenic and metastatic progenitor cells." Oncogene 25: 1696-1708, 2006.
Prince, et al. "Identification of a subpopulation of cells with cancer stem cell properties in head and neck squamous cell carcinoma." Proceedings of the National Academy of Sciences 104:973-978, 2007.
Reya, et al. "Stem cells, cancer, and cancer stem cells." Nature 414: 105-111, 2001.
Ricci-Vitiani, et al. "Identification and expansion of human colon-cancer-initiating cells." Nature 445: 111-115, 2007.
Sato, et al. "Single Lgr5 stem cells build crypt villus structures in vitro without a mesenchymal niche." Nature 459: 262-265, 2009.
Schatton, et al. "Identification of cells initiating human melanomas." Nature 451: 345-349, 2008.
Singh, et al. "Identification of human brain tumour initiating cells." Nature 432: 396-401, 2004.
Vermeulen, et al. "Wnt activity defines colon cancer stem cells and is regulated by the microenvironment." Nature Cell Biology 12: 468-476, 2010.
Wu, et al. "Side population cells isolated from mesenchymal neoplasms have tumor initiating potential." Cancer Research 67: 8216-8222, 2007.
Fang et al., "A Tumorigenic Subpopulation with Stem Cell Properties in Melanomas," Cancer Res., vol. 65:9328-9337, 2005.
Perego et al., "Heterogeneous Phenotype of Human Melanoma Cells with In Vitro and In Vivo Features of Tumor-Initiating Cells," J. Invest. Dermatol., vol. 130:1877-1886, 2010.
Thenappan et al., "New Therapeutics Targeting Colon Cancer Stem Cells," Curr. Colorectal Cancer Rep., vol. 5:209-216, 2009.
Advisory Action dated Sep. 3, 2015 for U.S. Appl. No. 13/878,181 (4 pages).
Request for Continued Examination, submitted Sep. 23, 2015, in U.S. Appl. No. 13/878,181 (2 pages).

(56) References Cited

OTHER PUBLICATIONS

Martin et al., "Expression of the Transcription Factors Snail, Slug, and Twist and Their Clinical Significance in Human Breast Cancer," *Ann. Surg. Oncol.*, vol. 12:1-9, 2005.
Final Office action dated Apr. 24, 2015 for U.S. Appl. No. 13/878,181 (26 pages).
Amendment and Response after Final Action, submitted Aug. 21, 2015, in U.S. Appl. No. 13/878,181 (9 pages).
Hirsch et al., "LGR5 positivity defines stem-like cells in colorectal cancer," *Carcinogenesis* 35(4):849-858, 2014.
Office Action dated Mar. 25, 2016 in U.S. Appl. No. 13/878,181, filed Jul. 5, 2013 (21 pages).
Pollard et al., "Glioma Stem Cell Lines Expanded in Adherent Culture Have Tumor-Specific Phenotypes and Are Suitable for Chemical and Genetic Screens," *Cell Stem Cell* 4(6):568-580, 2009.
Kim et al., "Role of lymphocyte-specific protein tyrosine kinase (LCK) in the expansion of glioma-initiating cells by fractionated radiation," *Biochem Biophys Res Commun* 402:631-636, 2010.
Final Office Action dated Dec. 1, 2016, issued in U.S. Appl. No. 13/878,181 (18 pages).
Ito et al., "NOD/SCID/$\gamma_c^{null}$ mouse: an excellent recipient mouse model for engraftment of human cells," *Blood* 100(9):3175-3182, 2002.
Almagro and Fransson, "Humanization of antibodies" *Front Biosci* 13:1619-1633, 2008.
Cobleigh, "Other Options in the Treatment of Advanced Breast Cancer," *Seminars Oncol* 38(Suppl 2):S11-S16, 2011.
Fuchs et al., "Irinotecan in the treatment of colorectal cancer," *Cancer Treat Rev* 32(7):491-503, 2006.
Hamada et al., "Liver metastasis models of colon cancer for evaluation of drug efficacy using NOD/Shi-scid IL2R$\gamma^{null}$ (NOG) mice," *Int J Oncol* 32(1):153-159, 2008.
Invivogen, "Immunoglobulin G—Review," http://www.invivogen.com/review-antibody-generation, 2011 (2 pages).
Office Action issued for U.S. Appl. No. 13/878,181 dated Jan. 17, 2018 (24 pages).
Office Action dated Aug. 8, 2019 in connection with U.S. Appl. No. 13/878,181 (15 pages).
Botchkina et al., "Phenotypic Subpopulations of Metastatic Colon Cancer Stem Cells: Genomic Analysis," *Cancer Genomics Proteomics* 6(1):19-29, 2009.
DeRycke et al., "Nectin 4 Overexpression in Ovarian Cancer Tissues and Serum," *Am J Clin Pathol* 134: 835-845, 2010.
Enfortumab Vedotin (ASG-22ME) | ADC Review, In Press Media Group, Jul. 29, 2016: http://adcreview.com/enfortumab-vedotin-asg-22me-formerly-ags-22m6e-clinical-trials/ (1 page).
Fabre-Lafay et al., "Nectin-4, a New Serological Breast Cancer Marker, Is a Substrate for Tumor Necrosis Factor-a-converting Enzyme (TACE)/ADAM-17," *J Biol Chem* 280(20): 19543-19550, 2005.
Satpayev et al., "Abstract 2832: Development of AGS-22M6E, a novel antibody drug conjugate (ADC) targeting Nectin-4 for the treatment of solid tumors," *Cancer Res* 71(8 Supplement), Apr. 2011.
Takano et al., "Identification of Nectin-4 Oncoprotein as a Diagnostic and Therapeutic Target for Lung Cancer," *Cancer Res* 69(16): 6694-6703, 2009.
Final Office Action dated Sep. 7, 2018, issued in U.S. Appl. No. 13/878,181 (17 pages).
Zhou et al., "Internalizing Cancer Antibodies from Phage Libraries Selected on Tumor Cells and Yeast-Displayed Tumor Antigens," *J Mol Biol* 404(1):88-99, 2010.
U.S. Appl. No. 16/994,388.
Kirchner and Brabletz "Patterning a Nuclear β-Catenin Expression in the Colonic Adenoma-Carcinoma Sequence," *American Journal of Pathology*, 157(4):1113-1121 (2000).
Brabletz et al. "Migrating cancer stem cells—an integrated concept of malignant tumour progression," *Nature Reviews Cancer*, 5:744-749 (2005).
Dalerba et al. "Cancer Stem Cells: Models and Concepts," *The Annual Review of Medicine*, 58:267-284 (2007) published online Sep. 26, 2006.
Fujii et al. "Establishment and characterization of in vivo human tumor models in the NOD/SCID/$\gamma_c^{null}$ mouse," *Pathology International*, 58:559-567 (2008).
International Search Report of PCT/JP2010/073266 (dated Mar. 18, 2011).
U.S. Appl. No. 16/944,388, US 2020-0385686-A1.
U.S. Appl. No. 16/913,341, US 2020/0325222-A1.

* cited by examiner

PLR233

| | Anti-Human HLA-ABC Ab | Anti-Mouse MHC-I Ab (Not react with Human) |
|---|---|---|
| ANTIBODY− |  |  |
| ANTIBODY+ |  |  |

10% ARE DERIVED FROM MOUSE

WELL-DIFFERENTIATED ADENOCARCINOMA

ARROWHEAD:
LOW DIFFERENTIATED DUCT

MODERATE-DIFFERENTIATED ADENOCARCINOMA

DOTTED LINE: BUDDING IMAGE

METHOD FOR SEARCHING AND SCREENING FOR TARGET OF ANTI-CANCER AGENT USING NON-HUMAN ANIMAL MODEL HAVING NOG ESTABLISHED CANCER CELL LINE TRANSPLANTED THEREIN

CROSS REFERENCE TO RELATED APPLICATIONS

This is the U.S. National Stage of International Application No. PCT/JP2010/073266, filed Dec. 24, 2010, which in turn claims the benefit of Japanese Patent Application No. 2009-295426, filed Dec. 25, 2009.

TECHNICAL FIELD

The present invention relates to non-human animal models of cancer pathology, which mimic the hierarchical organization of human cancer tissues with cancer stem cells at the top of the hierarchy, reproduce the cancer progression process, and enable assessment of their biological properties. The present invention also relates to methods of screening for anti-cancer agents and methods for assessing the pharmacological effects of test substances, which use the non-human animal model or an in vitro culture system of an NOG-established cancer cell line, which is established by transplanting human tumor tissues into severely-immunodeficient NOD/SCID/gamma(c)(null) (NOG) mice.

BACKGROUND ART

Human tumor cells show various tissue structures, and such tissues are known to have a hierarchical organization with cancer stem cells at the top of the hierarchy (Non-patent Document 1). For example, it is known that colon cancer is roughly subdivided into two layers: first an area with differentiated colon epithelium-like cells having a glandular structure, and second an invasive area with cells having a tendency to differentiate into mesenchymal cells (Non-patent Documents 2 and 3). Such findings were obtained based on knowledge accumulated through a vast amount of morphological observations of human colon cancer tissues. However, animal models that mimic the hierarchical organization of cancer tissues are rare. Thus, little is understood about the process leading to the formation of the hierarchical organization of cancer tissues and the involvement of cancer stem cells in this process.

Meanwhile, it has recently been shown that NOG-established cancer cell lines, which are established by transplanting human tumor tissues into severely-immunodeficient NOD/SCID/gamma(c)(null) (NOG) mice, form tissue structures similar to those of human cancer tissues (Non-patent Document 4).

However, useful animal models were unavailable to morphologically observe the process leading to the formation of the hierarchical organization of cancer cell lines in vivo or to elucidate the involvement of cancer stem cells in the formation process. Use of animal models of cancer pathology that reflect a human cancer is known to give results closer to human clinical data when it comes to developing or assessing pharmaceutical agents for treating or preventing cancer, anti-cancer agent screening or assessment of pharmacological effects of test substances. Under these circumstances, there was a need for a non-human animal model exhibiting the cancer pathology more similar to that of a human cancer. Furthermore, there was a need for an in vitro cell culture system that exhibits cell morphology more similar to that of human cancer pathology.

PRIOR ART DOCUMENTS

Non-Patent Documents

[Non-patent Document 1] Dalerba P. et al., Annu Rev Med. 2007; 58: 267-284
[Non-patent Document 2] Brabletz T. et al, Nat Rev Cancer. 2005; 5: 744-749
[Non-patent Document 3] Kirchner T. v, Am J. Pathol. 2000; 157: 1113-1121
[Non-patent Document 4] Fujii E. et al, Pathol Int. 2008; 58: 559-567

SUMMARY OF THE INVENTION

Problems to be Solved by the Invention

An objective of the present invention is to provide non-human animal models of cancer pathology, which mimic the hierarchical organization of human cancer tissues, cancer progression process, and biological properties thereof. Another objective of the present invention is to provide methods of searching for anti-cancer agent targets, which use the non-human animal model or an in vitro culture system of an NOG-established cancer cell line, which is established by transplanting human tumor tissues into severely-immunodeficient NOD/SCID/gamma(c)(null) (NOG) mice. Still another objective of the present invention is to provide methods of screening for anti-cancer agents that are effective in preventing or treating cancer, which use the non-human animal model or the in vitro culture system of an NOG-established cancer cell line. Yet another objective of the present invention is to provide methods for assessing the preventive or therapeutic effect of test substances against human cancer, which use the non-human animal model or the in vitro culture system of an NOG-established cancer cell line.

Means for Solving the Problems

The present inventors conducted dedicated studies to achieve the objectives described above.

The present inventors predicted that the process leading to the formation of hierarchical organization, the involvement of cancer stem cells in the process, and their biological properties may be elucidated through morphological observation of tissue structures after transplanting NOG mice with NOG-established cancer cell lines, which are established by transplanting human tumor tissues into severely-immunodeficient NOG mice. Based on this prediction, the present inventors conducted the studies described below.

First, NOG-established cancer cell lines derived from colon cancer, stomach cancer, breast cancer, lung cancer, and pancreatic cancer were morphologically observed after the transplantation into the NOG mouse. Observations revealed an area where the human cancer tissue took an epithelium-like structure, and an invasive area where some of the cells have a mesenchymal phenotype (FIGS. 1 to 4).

Furthermore, the hierarchical organization was remarkably similar to that of donors' human cancer tissues, and time-dependent changes were observed during the cancer progression process leading to the formation of the hierarchical organization. In addition, when observing cell lines established from donors' tumors of different tissue types over time, it showed that: cells of each cell line formed tissue morphologies resembling the donor's tumor after going through a progression process with changes unique to the cell line (Table 1); this was repeatedly reproduced (FIG. 5); and during the process cancer stem cells changed their biological state in a time-dependent manner (FIGS. 6 and 7). Although the existence of such transitional cancer stem cells has been predicted to some degree in human colon cancer, the present invention empirically demonstrated, for the first time, the existence of transitional cancer stem cells and their involvement in the hierarchical organization in tumor tissues (FIG. 8) by using NOG mice and the established cancer cell lines. As described above, since each cell line repeatedly undergoes a uniquely changing progression process, this partly revealed one biological property of cancer stem cells, i.e., that cancer stem cells in situ have their own unique final destination of differentiation (FIG. 5 and Table 1).

Furthermore, the present inventors monitored time-dependent changes of cancer stem cells over two generations, and revealed that cells which once lost their characteristics as cancer stem cells and differentiated in the first generation newly acquired stem cell characteristics in the second generation, i.e., the biological property of stem cell plasticity (FIG. 9).

In recent years, decrease in expression level of proteins such as P53 have been demonstrated to be involved in the phenomenon called reprogramming by which stem cells acquire pluripotency. Therefore, the present inventors carried out immunostaining for the P53 protein and revealed that the expression level of P53 protein was reduced even in the cancer stem cells detected with the models of the present invention (FIG. 10). This finding demonstrates that the models of the present invention faithfully mimic the cancer stem cell biological property of reprogramming.

Furthermore, it has been recently pointed out that fibroblasts in the tumor stroma may play an important role in tumor growth/progression. In some tumors, the fibroblasts are predicted to be derived from the tumors themselves through complete epithelial-mesenchymal transition (complete-EMT) (Radisky D C, et al., J Cell Biochem. 2007; 101: 830-9). In the present invention, time-course observations after transplantation of NOG-established cancer cell line into mice revealed that the detected fibroblasts were derived not from the host (mouse) but from the transplanted human tissues. This demonstrates that the models of the present invention also mimic the formation of the hierarchical organization including tumor stroma formation (FIGS. 11 and 12). In addition, by using NOG-established cancer cell lines of the present invention, the present inventors succeeded in preparing cell models resistant to anti-cancer agents (FIG. 13).

As described above, time-course observations of NOG mice transplanted with NOG-established cancer cell lines revealed that:
(1) the present invention enables preparation of animal models that repeatedly mimic the hierarchical organization of donors' human cancer tissues;
(2) unique cancer stem cells, which have a property responsible for the formation of each hierarchical organization, are observed in the models of the present invention, and the models mimic the biological properties of cancer stem cells; and
(3) the present invention enables preparation of in vivo animal models that enable observation of the process leading to the transition of cancer cells into tumor stroma-forming fibroblasts through complete-EMT during the process that mimics the formation of the hierarchical organization. These properties could also be mimicked by the in vitro culture system using NOG-established cancer cell lines.

Next, since the novel model animals with the properties described above could be prepared, the present inventors tested the applicability of the models as novel methods of searching for anti-cancer agent targets and screening methods therefor.

A possible method of searching for novel anti-cancer agent targets is as follows:
tissue pieces having tissue structures characteristically seen in the progression process in each area (starting from the same cell line) are collected by laser microdissection (LMD); the mRNA expression is assessed to find genes whose expression varies depending on the process, tissue structure, or biological properties thereof.

Since a gene found by the above-described methods, or a protein encoded by the gene, is predicated to contribute to the cancer progression process, an inhibitor of the gene or protein is expected to serve as target for a novel anti-cancer agent that inhibits the cancer progression process.

Meanwhile, a possible novel screening method for assessing pharmaceutical agents is to assess whether a particular step of the cancer progression process is inhibited or a biological property characteristic of cancer stem cells is modulated by administering a pre-existing anti-cancer agent (for example, fluorouracil or irinotecan) to a model of the present invention, focusing attention on the cancer progression process, which can be monitored through the observation of time-dependent changes in the models of the present invention. When this example is applied to the screening for novel anti-cancer agents, the models of the present invention enable identification of the specific biological property or the cancer progression process on which a particular anti-cancer agent acts. Thus, such screening is expected to have greater predictive performance from a clinical viewpoint.

Specifically, the present inventors succeeded in preparing non-human animal models exhibiting cancer pathology more similar to human cancer and in vitro cell culture systems of NOG-established cancer cell lines where the cell morphologies are more similar to those in human cancer. The present inventors thus completed the present invention.

More specifically, the present invention provides:
[1] a non-human animal model, which is obtained by transplanting, into a non-human animal of the same or different species, an NOG-established cancer cell line established by transplanting a human tumor tissue into a severely-immunodeficient NOD/SCID/gamma(c)(null) (NOG) mouse;
[2] the non-human animal model of [1], which mimics hierarchical organization or cancer progression process of a human cancer tissue;
[3] the non-human animal model of [1], which enables
  detection of a unique cancer stem cell having a characteristic for mimicking hierarchical organization and cancer progression process of a human cancer tissue, and,
  testing of a biological property of the human cancer tissue;
[4] the non-human animal model of [1], which enables observation of the process leading to transition of a cancer cell into a tumor stroma-forming fibroblast through complete epithelial-mesenchymal transition (complete-EMT) during the process that mimics hierarchical organization of a human cancer tissue;
[5] a non-human animal model, which enables assessment of the cause of anti-cancer agent resistance by administering an anti-cancer agent into the non-human animal model of any one of [1] to [4], and assessing, as an indicator, hierarchical organization, cancer progression process, or biological property of a cancer cell, or transition through complete epithelial-mesenchymal transition (complete-EMT);

[6] the non-human animal model of any one of [1] to [4], wherein the human tumor tissue is derived from colon cancer, stomach cancer, breast cancer, lung cancer, or pancreatic cancer;

[7] a method of searching for an anti-cancer agent target, wherein assessment is carried out, using as an indicator, hierarchical organization, cancer progression process, or biological property of a cancer cell in a non-human animal model transplanted with an NOG-established cancer cell line or in an in vitro culture system of an NOG-established cancer cell line;

[8] the method of searching for an anti-cancer agent target of [7], which comprises the steps of:
(1) preparing a non-human animal model by transplanting an NOG-established cancer cell line into a non-human animal;
(2) collecting a tissue piece that exhibits a biological property or a tissue structure characteristically seen in the cancer progression process in each area, when starting from a cell line same as the NOG-established cancer cell line;
(3) assessing the expression of DNA, RNA, or protein in the collected tissue piece of (2); and
(4) identifying a gene or protein that changes in a manner dependent of the hierarchical organization, cancer progression process, or biological property of a cancer cell in the tissue piece;

[9] the method of searching for an anti-cancer agent target of [7], which comprises the steps of:
(1) culturing in vitro an NOG-established cancer cell line to mimic a biological property or a structure characteristic of each cancer progression process;
(2) assessing the expression of DNA, RNA, or protein in a cultured cell mimicking a specific structure; and
(3) identifying a gene or protein in the cultured cell that changes in a manner dependent of the hierarchical organization, cancer progression process, or biological property of a cancer cell;

[10] a method of screening for an anti-cancer agent, wherein assessment is carried out, using as an indicator, hierarchical organization, cancer progression process, or biological property of a cancer cell in a non-human animal model transplanted with an NOG-established cancer cell line or in an in vitro culture system of an NOG-established cancer cell line;

[11] the method of screening for an anti-cancer agent of [10], which comprises the steps of:
(1) preparing a non-human animal model by transplanting an NOG-established cancer cell line into a non-human animal;
(2) administering a test substance to the non-human animal model of (1);
(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or biological property of a cancer cell in the tissue piece; and
(5) identifying the formation of the hierarchical organization, cancer progression process, or biological property of a cancer cell, which is inhibited by the test substance;

[12] the method of screening for an anti-cancer agent of [10], which comprises the steps of:
(1) culturing in vitro an NOG-established cancer cell line to mimic a biological property or a structure characteristic of each cancer progression process;
(2) treating the cultured cell of (1) with a test substance;
(3) monitoring a time-dependent change of hierarchical organization, cancer progression process, or biological property of a cancer cell in the cultured cells; and
(4) identifying the hierarchical organization formation, cancer progression process, or biological property of a cancer cell, which is inhibited by the test substance;

[13] the method of screening for an anti-cancer agent of [10], which comprises the steps of:
(1) preparing a non-human animal model by transplanting an NOG-established cancer cell line into a non-human animal;
(2) administering a test substance to the non-human animal model of (1);
(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or biological property of a cancer cell in the tissue piece; and
(5) identifying a test substance that inhibits the formation of the hierarchical organization, cancer progression process, or biological property of a specific cancer cell;

[14] the method of screening for an anti-cancer agent of [10], which comprises the steps of:
(1) culturing in vitro an NOG-established cancer cell line to mimic a biological property or a structure characteristic of each cancer progression process;
(2) treating the cultured cells of (1) with a test substance;
(3) monitoring a time-dependent change of hierarchical organization, cancer progression process, or biological property of a cancer cell among the cultured cells; and
(4) identifying a test substance that inhibits hierarchical organization formation, cancer progression process, or biological property of a specific cancer cell;

[15] a method for assessing a pharmaceutical agent for treating or preventing a human cancer, wherein assessment is carried out, using as an indicator, hierarchical organization, cancer progression process, or biological property of a cancer cell in a non-human animal model transplanted with an NOG-established cancer cell line or in an in vitro culture system of an NOG-established cancer cell line;

[16] the method of [15] for assessing a pharmaceutical agent for treating or preventing a human cancer, which comprises the steps of:
(1) preparing a non-human animal model by transplanting an NOG-established cancer cell line into a non-human animal;
(2) administering a test substance to the non-human animal model of (1);
(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or biological property of a cancer cell in the tissue piece; and
(5) identifying the formation of the hierarchical organization, cancer progression process, or biological property of a cancer cell, which is inhibited by the test substance;

[17] the method of [15] for assessing a pharmaceutical agent for treating or preventing a human cancer, which comprises the steps of:
(1) culturing in vitro an NOG-established cancer cell line to mimic a structure characteristic of each cancer progression process or a biological property thereof;
(2) treating the cultured cell of (1) with a test substance;
(3) monitoring a time-dependent change of the hierarchical organization, cancer progression process, or biological property of a cancer cell among the cultured cells; and
(4) identifying the formation of the hierarchical organization, cancer progression process, or biological property of a cancer cell, which is inhibited by the test substance; and

[18] a method of using a non-human animal transplanted with an NOG-established cancer cell line or an NOG-established cancer cell line as a cancer model animal or cell line which mimics hierarchical organization, cancer progression process, or biological property of a cancer cell.

Effects of the Invention

The present invention provides non-human animal models of cancer pathology more similar to human cancer and in vitro cell culture systems whose cell morphologies are more similar to those in the human cancer pathology. A result closer to human clinical data is expected be obtained by screening for anti-cancer agents or assessing the pharmacological effects of test substances using an animal model of cancer pathology or a cancer cell culture system that more closely reflects human cancer.

MODE FOR CARRYING OUT THE INVENTION

Figure 1:
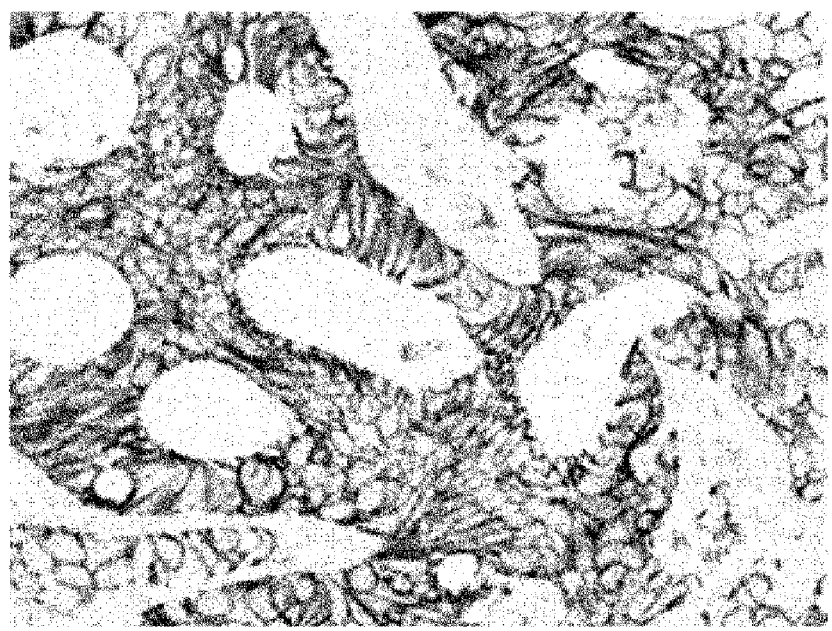
FIG. 1 is a photograph showing an epithelium-like proliferation area in colon cancer. The glandular structure is observed, and E-cadherin is expressed on the whole cell surface.

The present invention relates to non-human animal models of cancer pathology, which can be effectively used for developing pharmaceutical agents for treating or preventing human cancer, and cell culture systems that exhibit in vitro cell morphology more similar to that in a cancer pathology. Specifically, the present invention relates to non-human animal models obtained by transplanting an NOG-established cancer cell line (established by transplanting human cancer tissues into severely-immunodeficient NOD/SCID/gamma(c)(null) (NOG) mice) into non-human animals of the same or a different species, as well as in vitro culture systems of the NOG-established cancer cell lines.

The non-human animal models of the present invention may mimic the hierarchical organization of cancer tissues, cancer progression process, and biological properties thereof, which are unique to pathology of a human cancer. In the present invention, types of target cancers are not particularly limited, but preferably include, for example, colon cancer, stomach cancer, lung cancer, breast cancer, and pancreatic cancer.

Herein, the "hierarchical organization of cancer tissues, which is unique to human cancer pathology" includes a two-layer structure having an area with a glandular structure consisting of cells with epithelial-like differentiation and an invasive area with cells having a tendency to differentiate into mesenchymal cells.

In the above-described epithelium-like glandular area, E-cadherin is expressed on whole cell surface. The expression of E-cadherin can be tested using an anti-E-cadherin antibody.

The above-described invasive area exhibits characteristic morphologies: budding, cluster of tumor cells, dissociated single tumor cells, and reconstruction of tubules. Cells in the invasive area undergo partial-EMT leading to partial loss of the epithelial nature; lack E-cadherin expression at their contact surface with the stromal cells; and express fibronectin, which is normally not expressed on epithelium-like cells.

Furthermore, cancer stem cells, which are slow-cycling cells, can be detected in both the above-described epithelium-like glandular area and invasive area. Whether cancer stem cells are present in these areas can be assessed by using a cell proliferation marker (for example, continuous BrdU labeling and Ki67 staining), a cancer stem cell marker (for example, Lgr5 staining), or the like.

In addition, the present invention enables time-course and simultaneous observation of both the presence of cancer stem cells and the mimicking of the hierarchical organization of cancer tissues, cancer progression process, or biological properties thereof. This helps to elucidate the hierarchical organization and cancer progression process, i.e., how the cancer tissue-specific structure is formed originating from cancer stem cells.

More specifically, in the high stress environment at the early stage after transplantation, mainly surviving are the cancer stem cells and their progenitor cells. After the growth phase starts, gland-forming cancer cells emerge in the above-described epithelium-like glandular area. Meanwhile, slow-cycling cancer stem cells and their progenitor cells are maintained and become responsible for further expansion of the epithelium-like glandular area. On the other hand, in the above-described invasive area, partial-EMT cells such as cluster of tumor cells and dissociated single tumor cells emerge among cells that managed to survive under the high stress environment at the early stage after transplantation. These slow-cycling cancer stem cells are migrating cells since they have undergone partial-EMT, and expand their area while contributing to cancer invasion/dissemination and such. Furthermore, when reaching a specific environment, some partial-EMT cells undergo a so-called mesenchymal-epithelial transition (MET) there. Due to MET, partial-EMT cells which once lost the epithelial nature acquire this epithelial nature again, and then newly form epithelium-like glandular structures there.

In the present invention, the "cancer progression process unique to pathology of a human cancer" includes, for example, the following processes depending on the differentiation status of cancer cells.

In the case of well-differentiated cancer, the major process is an epithelium-like proliferation process (epithelial duct-forming pattern). In the case of moderately-differentiated cancer, the major process is an invasive proliferation process (invasive EMT pattern), while including an epithelium-like proliferation process (epithelial duct-forming pattern). In the case of poorly-differentiated cancer, the major process is an invasive proliferation process (invasive EMT pattern).

Examples that the present invention "enables assessment for the biological properties of cancer stem cells" include those described below.

Since each cell line repeatedly undergoes a uniquely changing progression process, cancer stem cells in situ show the biological property of having their own unique final destination of differentiation.

When following the transition of cancer stem cells over two generations, cells that lost their properties as cancer stem cells and differentiated in the first generation again acquire the properties as stem cells in the second generation, i.e., the biological property so-called stem cell plasticity.

A decreased expression of P53 protein is known to be involved in the stem cells' biological property of the acquirement of the pluripotency, i.e., reprogramming. This property is mimicked by cancer stem cells found in the models of the present invention.

Furthermore, the animal models of the present invention mimic the process of transition of cancer cells into tumor stroma-forming fibroblasts through complete epithelial-mesenchymal transition (complete-EMT). The transition into fibroblasts can be tested by IHC staining. The transition into human-specific fibroblasts can be assessed by IHC staining for human-specific $\beta 2$ microglobulin.

The animal models of the present invention enable observation of an above-described process unique to the type of target cancer or the status of cancer progression.

Unique cancer stem cells which have the properties of mimicking the above-described hierarchical organization of human cancer tissues and cancer progression process can be detected in the animal models of the present invention.

Animals that can be used to prepare the animal models of the present invention include, for example, non-human mammals commonly used in conventional experiments such as mice, nude mice, rats, nude rats, guinea pigs, hamsters, rabbits, dogs, and monkeys. Preferred animals include, for example, rodents such as mice, nude mice, rats, nude rats, guinea pigs, hamsters, and rabbits. For the convenience of breeding and manipulation, more preferred animals include, for example, mice, nude mice (for example, NOD/SCID/gamma(c)(null) (NOG) mice), rats, and nude rats.

An animal (recipient animal) to be transplanted with an NOG-established cancer cell line may be of the same or different species from the severely-immunodeficient NOD/SCID/gamma(c)(null) (NOG) mouse (donor animal) with which an NOG-established cancer cell line is established. From an immunological viewpoint, the animals are preferably of the same species. However, when immunodeficient animals such as nude mice or nude rats are used, the animals may be of different species.

The methods for preparing the animal models of the present invention are described below.

The animal models of the present invention can be prepared by transplanting NOG-established cancer cell lines established by transplanting human tumor tissues into severely immunodeficient NOD/SCID/gamma(c)(null) (NOG) mice as donor animals, subcutaneously into recipient animals, or into their various body cavities, or various organs.

NOG-established cancer cell lines to be transplanted into recipient animals can be collected and established from the NOG mice. The age of such NOG mice can be selected depending on the type of established cancer cell line to be transplanted and the species of recipient animal.

The age of recipient animals is, for example, preferably 4 to 100 weeks old when they are mice, nude mice, SCID mice, NOD-SCID mice, NOG mice, rats, or nude rats.

Specifically, the animal models of the present invention can be prepared by the following method. First, an NOG-established cancer cell line (Fujii E. et al., Pathol Int. (2008) 58: 559-567), which is established by transplanting human-derived cancer cells into NOG mice and passaging, is transplanted into recipient animals. Subcutaneous transplantation is preferred as a transplantation site, because it is convenient to perform. However, transplantation sites are not particularly limited, and an appropriate transplantation site is preferably selected depending on the animal to be used. Meanwhile, the techniques for transplanting an NOG-established cancer cell line are not particularly limited; it is possible to use conventional transplantation techniques.

After transplantation, the model animals of the present invention may be reared under conventional or sterile conditions, if needed. The rearing conditions are not limited, but specifically include, for example, the conditions of: temperature of 20 to 26° C., humidity of 30 to 70%; feed and water: free intake; light cycle: a 12-hour light-dark cycle.

The period of animal rearing is not particularly limited; in the case of mice, nude mice, rats, or nude rats, it is preferable to rear the animals for three or more days, preferably 28 or more days after transplantation.

By rearing the transplanted animals for a certain period, the transplanted NOG-established cancer cell line grows and differentiates into tissues having the histological features of human tumor tissues at the transplantation site. As described above, the animal models of the present invention have tissues with features of human tumor tissues, and therefore can serve as animal models for human cancer pathology.

The cells are cultured by a culture method using an appropriate medium (D-MEM, MEM, RPMI1640, BME, D-MEM/F12, G-MEM, etc.) supplemented with appropriate additives (inactivated Fetal Bovine Serum, Penicillin, Streptomycin, Glucose, Sodium Hydrogen Carbonate, HEPES, L-Glutamine, Heparin, BSA, FGF, EGF, Transferrin, Insulin, Putrescin, Selenite, Progesterone, etc.) under conditions suitable for mammalian cell culture (for example, at 37° C. under 5% $CO_2$).

When the hierarchical organization, cancer progression process, or biological property of cancer cells observed in the model animals, or in the in vitro culture system of NOG-established cancer cell lines of the present invention, is used as an indicator for assessment, the model or in vitro culture system of the present invention can be applied to search for anti-cancer agent targets, screen for anti-cancer agents, or screen to assess pharmaceutical agents for treating or preventing human cancer.

The present invention relates to methods of searching for anti-cancer agent targets, which carry out an assessment, using as an indicator, the hierarchical organization, cancer progression process, or biological property of the cancer cells in a non-human animal model transplanted with an NOG-established cancer cell line or an in vitro culture system of an NOG-established cancer cell line.

In the methods of the present invention, when a non-human animal model transplanted with an NOG-established cancer cell line is used, the search for anti-cancer agent targets can be carried out via steps (1) to (4) described below:

(1) preparing a non-human animal model by transplanting an NOG-established cancer cell line into a non-human animal;

(2) collecting a tissue piece that exhibits a biological property or a tissue structure characteristically seen in the cancer progression process in each area, when starting from a cell line same as the NOG-established cancer cell line;

(3) assessing the expression of DNA, RNA, or protein in the collected tissue piece of (2); and (4) identifying a gene or protein that changes in a manner dependent of the hierarchical organization, cancer progression process, or biological property of a cancer cell in the tissue piece.

Alternatively, in the methods of the present invention, when the in vitro culture system of an NOG-established cancer cell line is used, the search for targets for anti-cancer agents can be carried out via steps (1) to (3) described below:

(1) culturing in vitro an NOG-established cancer cell line to mimic a biological property or a structure characteristic of each cancer progression process;

(2) assessing the expression of DNA, RNA, or protein in a cultured cell mimicking a characteristic structure; and (3) identifying a gene or protein in the cultured cell that changes in a manner dependent of the hierarchical organization, cancer progression process, or biological property of a cancer cell.

In the present invention, the structure of a tissue or cell line characteristic of a cancer progression process can be morphologically observed by HE staining and immunohistochemistry (IHC) of thin sections of tissue samples prepared by the AMeX method or the like. When the above-described hierarchical organization, cancer progression process, or biological property specific to a human tumor tissue is detected in a test tissue, the tissue is judged as a cancer-related tissue and is tested for the expression of DNAs, RNAs, or proteins. In the present invention, RNAs include, but are not limited to, mRNA and micro-RNA. Methods for testing the expression of a DNA, RNA, or protein are not particularly limited; testing can be done by conventional methods for assessing expression. For example, mRNA for each gene is extracted by conventional methods. The transcriptional level of each gene can be determined by Northern hybridization or RT-PCR using the mRNA as a template. Alternatively, the expression level of each gene can be measured using DNA array techniques. Furthermore, fractions containing the protein encoded by each gene may be collected by conventional methods. The expression of each protein can be detected by electrophoresis such as SDS-PAGE to determine the translational level of the gene. Alternatively, the expression of each protein can be detected by Western blotting using an antibody against the protein to determine the translational level of the gene.

The present invention relates to methods of screening for anti-cancer agents, which carry out assessment, using as an indicator, the hierarchical organization, cancer progression process, or biological property of cancer cells in a non-human animal model transplanted with an NOG-established cancer cell line or an in vitro culture system of an NOG-established cancer cell line.

In the methods of the present invention, when a non-human animal model transplanted with an NOG-established cancer cell line is used, the screening for anti-cancer agents can be carried out via steps (1) to (5) described below:

(1) preparing a non-human animal model by transplanting an NOG-established cancer cell line into a non-human animal;

(2) administering a test substance to the non-human animal model of (1);

(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or biological property of a cancer cell in the tissue piece; and
(5) identifying the formation of the hierarchical organization, cancer progression process, or biological property of a cancer cell, which is inhibited by the test substance.

In another embodiment, when the non-human animal model transplanted with an NOG-established cancer cell line is used, the screening for anti-cancer agents can be carried out via steps (1) to (5) described below:
(1) preparing a non-human animal model by transplanting an NOG-established cancer cell line into a non-human animal;
(2) administering a test substance to the non-human animal model of (1);
(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or biological property of a cancer cell in the tissue piece; and
(5) identifying a test substance that inhibits the formation of the hierarchical organization, cancer progression process, or biological property of a specific cancer cell.

Alternatively, in the methods of the present invention, when the in vitro culture system of an NOG-established cancer cell line is used, the screening for anti-cancer agents can be carried out via steps (1) to (4) described below:
(1) culturing in vitro an NOG-established cancer cell line to mimic a biological property or a structure characteristic of each cancer progression process;
(2) treating the cultured cell of (1) with a test substance;
(3) monitoring a time-dependent change of hierarchical organization, cancer progression process, or biological property of a cancer cell in the cultured cells; and
(4) identifying the hierarchical organization formation, cancer progression process, or biological property of a cancer cell, which is inhibited by the test substance.

In another embodiment, when the in vitro culture system of an NOG-established cancer cell line is used, the screening for anti-cancer agents can be carried out via steps (1) to (4) described below:
(1) culturing in vitro an NOG-established cancer cell line to mimic a biological property or a structure characteristic of each cancer progression process;
(2) treating the cultured cells of (1) with a test substance;
(3) monitoring a time-dependent change of hierarchical organization, cancer progression process, or biological property of a cancer cell among the cultured cells; and
(4) identifying a test substance that inhibits hierarchical organization formation, cancer progression process, or biological property of a specific cancer cell.

The "test substances" in the methods of the present invention are not particularly limited, and include, for example, single compounds such as natural compounds, organic compounds, inorganic compounds, proteins, peptides, and amino acids; as well as compound libraries, expression products of gene libraries, cell extracts, cell culture supernatants, products of fermentation microorganisms, marine organism extracts, plant extracts, prokaryotic cell extracts, unicellular eukaryote extracts, and animal cell extracts. These may be purified substances or crude substances such as extracts of plants, animals, or microorganisms. The methods for producing test substances are also not particularly limited; the substances may be isolated from natural materials, synthesized chemically or biochemically, or prepared by genetic engineering.

If needed, the above test samples can be used after appropriately labeling. Labels include, for example, radiolabels and fluorescent labels. The test samples include not only those described above, but also mixtures of several types of such test samples.

In the present invention, methods for administering a test substance to non-human model animals are not particularly limited. It is possible to appropriately select oral administration or parenteral administration such as subcutaneous, intravenous, local, transdermal, or enteral (rectal) administration depending on the type of test substance to be administered.

In the methods of the present invention, methods for treating cultured an NOG-established cancer cell line with a test substance are not particularly limited. Such a treatment can be carried out by adding a test sample to a cell culture medium or cell extract. When the test sample is a protein, the treatment can be carried out, for example, by introducing a vector carrying a DNA encoding the protein into an NOG-established cancer cell line or adding the vector to a cell extract of an NOG-established cancer cell line. Alternatively, it is possible to use, for example, a two hybrid method using yeast, animal cells, or the like.

After treatment, the test substance can be assessed by excising the transplanted tissue (tissues transplanted with an NOG-established cancer cell line) from the model animal and observing histological features of the transplanted tissue or by studying the histological features using a cell culture system.

Specifically, the test substance can be assessed by observing the hierarchical organization of the transplanted tissue or cancer cells in a culture system in a non-human animal model or an in vitro culture system of an NOG-established cancer cell line, to assess the characteristic of hierarchical organization formation unique to human cancer cells or to confirm an effect on the cancer progression process characteristic of a human cancer. The structure of tissue or cell line characteristic of the cancer progression process can be morphologically observed by HE staining and immunohistochemistry (IHC) of thin sections of tissue samples prepared by the AMeX method or the like.

More specifically, the above-described assessment of a test substance can be carried out by the following procedure: control non-human model animals or an NOG-established cancer cell line are prepared without administering the test substance; in the same manner as described above, the hierarchical organization of the transplanted tissue or cancer cells in a culture system are observed and the formation of the hierarchical organization unique to human cancer cells is checked; and the hierarchical organization of cancer cells is compared between the control animals and non-human model animals or NOG-established cancer cell lines administered with the test substance. In this case, when the hierarchical organization unique to human cancer cell is not observed in the non-human animal model or NOG-established cancer cell line administered with the test substance as compared to the control animals, or when the level of hierarchy is reduced, the test substance can be selected as an effective substance having a therapeutic or preventive effect against a human cancer.

More specifically, the above-described assessment of a test substance can also be carried out by the following procedure:

control non-human model animals or the NOG-established cancer cell line are prepared without administering the test substance, and in the same manner, the cancer progression process of the transplanted tissue or cancer cells in a culture system are observed and presence of a cancer progression process unique to human cancer cells is checked; and the cancer progression process of cancer stem cell is compared between the control animals and non-human model animals or NOG-established cancer cell lines administered with the test substance. In this case, when the cancer progression process unique to human cancer cells is not seen in the non-human animal model or NOG-established cancer cell line administered with the test substance as compared to the control animals, the test substance can be selected as an effective substance having a therapeutic or preventive effect against a human cancer.

In addition, more specifically, the above-described assessment of a test substance can be carried out by the following procedure:

control non-human model animals or the NOG-established cancer cell line are prepared without administering the test substance, and in the same manner, biological properties of cancer stem cells of the transplanted tissues or cancer cells in the culture system are observed and the presence of the properties unique to human cancer cells is checked; and the properties of cancer stem cells is compared between the control animals and non-human model animals or NOG-established cancer cell lines administered with the test substance. In this case, when the property unique to human cancer cells is not present in the non-human animal model or NOG-established cancer cell line administered with the test substance as compared to the control animal, the test substance can be selected as an effective substance having a therapeutic or preventive effect against a human cancer.

Substances effective for preventing or treating a human cancer, which are selected by the above-described screening methods, may be further assessed by other drug efficacy tests or safety tests, if needed, and/or by clinical tests with human cancer patients to select more effective therapeutic or preventive substances with a higher practical use.

Furthermore, such effective therapeutic or preventive substances selected can also be industrially produced by chemical synthesis or biochemical synthesis (fermentation), or using genetic manipulation based on the result of structural analyses thereof.

The present invention relates to screening methods for assessing pharmaceutical agents for treating or preventing human cancer, which carry out assessment using as an indicator the hierarchical organization or cancer progression process of the cancer cells in non-human model animals transplanted with an NOG-established cancer cell line.

When non-human model animals transplanted with an NOG-established cancer cell line are used in the methods of the present invention, pharmaceutical agents can be assessed via steps (1) to (5) described below:

(1) preparing a non-human animal model by transplanting an NOG-established cancer cell line into a non-human animal;
(2) administering a test substance to the non-human animal model of (1);
(3) collecting a tissue piece that exhibits a biological property or a tissue structure characteristically seen in the cancer progression process in each area, when starting from a cell line same as the NOG-established cancer cell line;
(4) monitoring a time-dependent change of hierarchical organization, cancer progression process, or a biological property of a cancer cell in the tissue piece; and
(5) identifying the formation of the hierarchical organization, cancer progression process, or biological property of a cancer cell, which is inhibited by the test substance.

Alternatively, when an in vitro culture system of NOG-established cancer cell lines is used in the methods of the present invention, pharmaceutical agents can be assessed via steps (1) to (4) described below:

(1) culturing in vitro an NOG-established cancer cell line to mimic a structure characteristic of each cancer progression process or a biological property thereof;
(2) treating the cultured cell of (1) with a test substance;
(3) monitoring a time-dependent change of hierarchical organization, cancer progression process, or biological property of a cancer cell among the cultured cells; and
(4) identifying the formation of the hierarchical organization, cancer progression process, or biological property of a cancer cell, which is inhibited by the test substance.

In the present invention, pharmaceutical agents can be assessed by administering a test substance of interest to an above-described non-human model animal or treating an in vitro culture system of an NOG-established cancer cell line with a test substance of interest, and testing whether administration of the test substance produces a preventive or ameliorating effect on the transplanted tissues (tissues transplanted with the NOG-established cancer cell line) or the culture system.

Specifically, the preventive or ameliorating effect of an administered test substance on the transplanted tissue or the culture system can be assessed by identifying or observing the morphology of hierarchical organization, the cancer progression process, or biological properties of cancer cells. The assessment can be carried out by observing the hierarchical organization of the transplanted tissues in the non-human animal model or of the cancer cells in an in vitro culture system of an NOG-established cancer line to verify the formation of the hierarchical organization characteristic of human cancer cells or an effect on the cancer progression process characteristic of a human cancer.

More specifically, the above-described assessment of a test substance can be carried out by the following procedure: control non-human model animals or NOG-established cancer cell line are prepared without administering the test substance, and in the same manner as described above, the transplanted tissues or cancer cells in the culture system are observed for the hierarchical organization of cancer cells and checked for the formation of the hierarchical organization unique to human cancer cell; and the hierarchical organization of cancer cells is compared between the control animals and non-human model animals or NOG-established cancer cell lines administered with the test substance. In this case, when the hierarchical organization unique to human cancer cell is not observed in the non-human animal model or NOG-established cancer cell line administered with the test substance as compared to the control animals, or when the level of hierarchy is reduced, the test substance administered to the test animal or with which the culture system is treated can be judged to have the preventive or therapeutic effect against the human cancer, and the level of the preventive or therapeutic effect can be evaluated based on the level of reduction.

Alternatively and more specifically, the above-described assessment of a test substance can be carried out by the following procedure:
control non-human model animals or NOG-established cancer cell line are prepared without administering the test substance, and in the same manner, the transplanted tissues or cancer cells in the culture system are observed for their cancer progression process and checked for the presence of a cancer progression process unique to human cancer cells; and the cancer progression process unique to cancer stem cells is compared between the control animals and non-human model animals or NOG-established cancer cell lines administered with the test substance. In this case, when the cancer progression process unique to human cancer cells is not present in the non-human animal model or NOG-established cancer cell line administered with the test substance as compared to the control animals, the test substance administered to the test animal or with which the culture system is treated can be judged to have a preventive or therapeutic effect against the human cancer, and the level of the preventive or therapeutic effect can be evaluated based on the level of advancement in the cancer progression process.

More specifically, the above-described assessment of a test substance can also be carried out by the following procedure:
control non-human model animals or NOG-established cancer cell line are prepared without administering the test substance, and in the same manner, the transplanted tissues or cancer cells in a culture system are observed for the biological properties of cancer stem cells and checked for the presence of a property unique to human cancer cells; and the property unique to cancer stem cells is compared between the control animals and non-human model animals or NOG-established cancer cell lines administered with the test substance. In this case, when the property unique to human cancer cells is not present in the non-human animal model or NOG-established cancer cell line administered with the test substance as compared to the control animals, the test substance administered to the test animal or with which the culture system is treated can be judged to have a preventive or therapeutic effect against the human cancer, and the level of the preventive or therapeutic effect can be evaluated based on the incidence of the properties.

The present invention relates to methods of using a non-human animal transplanted with an NOG-established cancer cell line or an NOG-established cancer cell line as a cancer model animal or cell line which mimics the hierarchical organization, cancer progression process, or biological property of cancer cells.

The hierarchical organization, cancer progression process, or biological property of cancer cells can be artificially or artifactually mimicked in vivo by transplanting an NOG-established cancer cell line into non-human animals. Thus, such non-human animals transplanted with the NOG-established cancer cell line can serve as very useful cancer model animals, for example, when assessing pharmaceutical agents, searching for candidate target molecules as pharmaceuticals or diagnostic agents, or assessing compounds or biological preparations that act on the candidate molecules using the hierarchical organization, cancer progression process, or biological property of cancer cells.

Furthermore, the hierarchical organization, cancer progression process, or biological property of cancer cells can be artificially or artifactually mimicked in vivo or in vitro by an NOG-established cancer cell line alone. Thus, the NOG-established cancer cell lines can serve as very useful cancer models, for example, when assessing pharmaceutical agents, searching for candidate target molecules as pharmaceutical agents or diagnostic agents, or assessing compounds or biological preparations that act on the candidate molecules using the hierarchical organization, cancer progression process, or biological property of cancer cells.

"Mimic" or "reproduce" means that the model mimics/reproduces to a level enough to achieve the objective depending on the model's purpose of use. Thus, it is not necessary to mimic/reproduce the in vivo events perfectly.

All prior art documents cited herein are incorporated herein by reference.

EXAMPLES

Hereinbelow, the present invention will be described more specifically with reference to the Examples, but it is not limited thereto.

Example 1

NOG-Established Cancer Cell Line Mimics Hierarchical Organization of Human Cancer Tissue (1) NOG-Established Cancer Cell Line and Staining Method The present inventors used NOG-established cancer cell lines that had been established so as to meet the criterion that human colon cancer, stomach cancer, lung cancer, breast cancer, or pancreatic cancer can be transplanted or passaged over three or more generations in NOG mice (Fujii E. et al., Pathol Int. 2008; 58: 559-567). In this Example, NOG-established cancer cell lines were subcutaneously transplanted into NOG mice. 28 days after transplantation, the mice were dissected, and the implants were excised and fixed with 4% paraformaldehyde at 4° C. for 16 to 24 hours. Then, the fixed samples were embedded and sliced into thin section samples by the AMeX method (Fujii E. et al., Pathol Int. 2008; 58: 559-567). The tissues were stained by HE and immunohistochemistry (IHC). Anti-E-cadherin antibody (DakoCytomation) and anti-fibronectin antibody (DakoCytomation) were used as a primary antibody. The visualization was carried out by LSAB method using DAB (DAB Map kit, Roche Diagnostics).

In addition, for in vitro culture, cell masses collected from mice were minced physically with scissors. Next, Collagenase/Dispase (Roche, Cat. No. 10 269 638 001) and DNaseI (Roche, Cat. No. 11 284 932 001) were added, and the cells were stirred at 37° C. for 30 minutes. Then, pipetting was repeated to prepare minced cells. The prepared cells were suspended in Cell Banker 1 (JUJI FIELD, Cat. No. BLC-1) and stored at −80° C. or below.

The cells prepared as described above were cultured in Medium 1 (RPMI1640, 10% Fetal Bovine Serum, Penicillin, Streptomycin) supplemented with Fetal Bovine Serum that had been inactivated by incubating at 56° C. for 30 minutes or more.

Spheroid preparation was carried out by suspending cells at $4 \times 10^5$ cells/ml in Medium 1 and plating 5 ml of the cells in 6-cm Hydro cell Dish (NUNC, Cat. No. 174912). After 3 to 6 days of incubation, spheroid formation was verified under a microscope. Following spheroid formation, the spheroid cells alone were collected by filtering all cells with 40-μm cell strainer (BD, Cat. No. 352340) and cultured in Medium 1.

As for a culture system to mimic the glandular structure, a stock solution of Matrigel Basement Membrane Matrix (BD, Cat. No. 354234) was added at 50 µl/well to 96-well plates. For coating, the 96-well plates were allowed to stand at 37° C. for 5 minutes. Next, the spheroid cells were added at 50 µl/well. Then, Matrigel Basement Membrane Matrix diluted to 20% with Medium 1 was added at 50 µl/well, and the plates were allowed to stand at 37° C. for 5 minutes. Finally, Medium 1 was added at 100 µl/well, and the cells were cultured until the glandular structure appeared.

(2) Results and Conclusions

Figure 2:
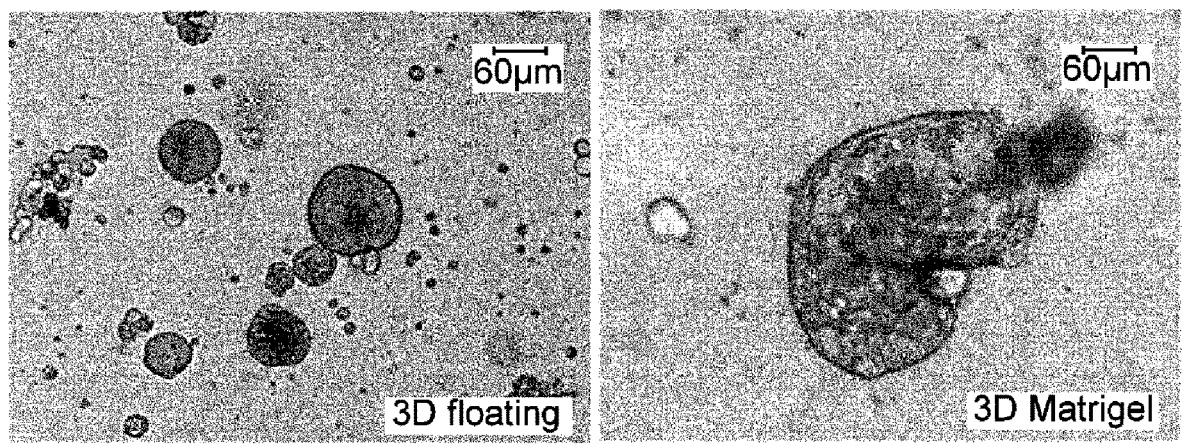
FIG. 2 shows photographs depicting an epithelium-like proliferation under in vitro culture conditions. Left panel: three-dimensional suspension culture; right panel: three-dimensional Matrigel culture. Formation of epithelium-like glandular structures is observed with the three-dimensional Matrigel culture. NOG-established colon cancer cell line was used.

The epithelium-like glandular area of human colon cancer tissue has been reported to be characteristic in that the cells express E-cadherin on their whole surface (Kirchner T. et al., Am J. Pathol. 2000; 157: 1113-1121). This characteristic was also observed in the NOG-established cancer cell line (FIG. 1). Furthermore, under the above-described in vitro condition, the spheroid-forming cells were demonstrated to mimic the glandular structure (FIG. 2).

Figure 3:
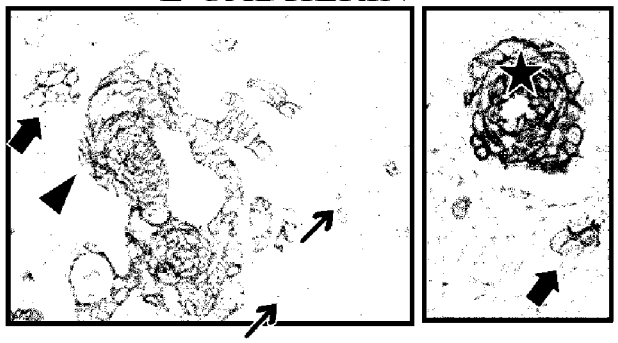
FIG. 3 shows photographs depicting an invasive area in colon cancer. E-cadherin expression has disappeared where each invasive area comes into contact with tumor stroma.

Meanwhile, the invasive area having the nature of mesenchymal cells, which are less differentiated, is known to exhibit characteristic morphologies such as budding, cluster of tumor cells, dissociated single tumor cells, and reconstruction of tubules. Cells in the invasive area have been said to undergo partial-EMT leading to a partial loss of the epithelial nature. It is known that the cells lack E-cadherin expression at their contact surface with the stroma and express fibronectin which is normally not expressed on epithelium-like cells (Kirchner T. et al., Am J. Pathol. 2000; 157: 1113-1121). In the present invention, these features were mimicked in the tumor that resulted from transplantation of an NOG-established colon cancer cell line (FIG. 3).

Figure 4:
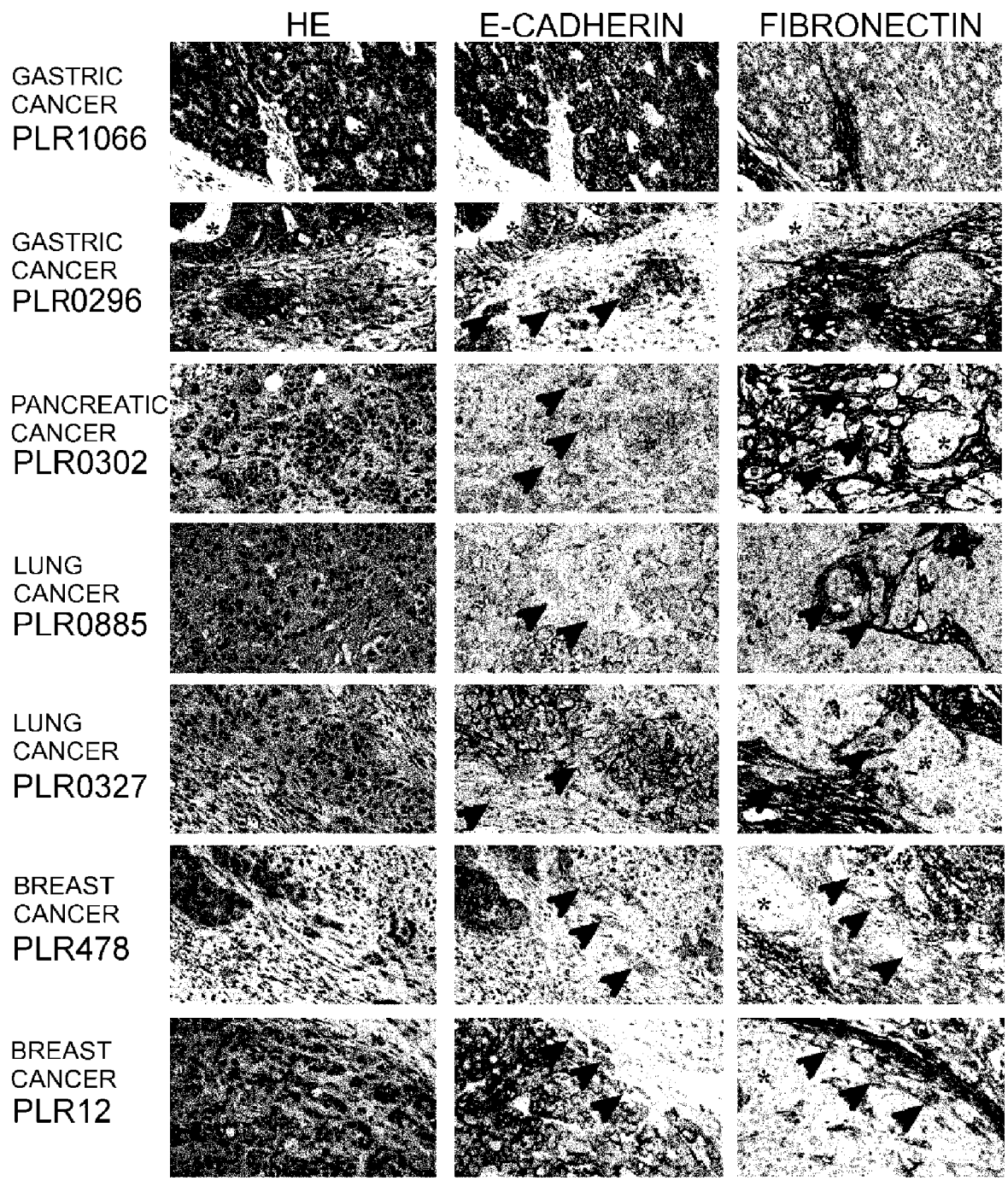
FIG. 4 shows photographs depicting an epithelial area and an invasive area in other types of cancers. These photographs indicate epithelium-like areas (*) where E-cadherin is present on the whole cell surface and invasive areas where E-cadherin has partially disappeared and fibronectin-positive cells are detected (areas indicated by arrow).

Similar epithelium-like areas and invasive areas were also observed in stomach cancer, lung cancer, breast cancer, and pancreatic cancer (FIG. 4).

The above-described results demonstrate that NOG-established cancer cell lines mimic the hierarchical organization of human cancer tissues.

Example 2

NOG-Established Cancer Cell Line Mimics the Process Leading to the Formation of the Hierarchical Organization Characteristic of Donor's Human Cancer Tissues (1) NOG-Established Cancer Cell Line and Staining Method Each NOG-established cancer cell line whose tissue morphology was (1) well-differentiated adenocarcinoma, (2) moderately-differentiated adenocarcinoma, or (3) poorly-differentiated adenocarcinoma in the donors' human colon cancer were subcutaneously transplanted into NOG mice. The mice were dissected 3, 7, 14, 17, or 21 days after transplantation, and HE staining and IHC were carried out in the same manner as described above to morphologically determine the ratio between the epithelium-like area and invasive area.

Furthermore, with respect to stomach cancer, colon cancer, and lung cancer, HE-stained samples from donors' cancer tissues and NOG-established cancer cell lines were observed to verify whether they repeatedly mimic the tissue organization.

(2) Results and Conclusions

The present invention demonstrated that:
in the unique cancer progression process leading to the formation of the hierarchical organization equivalent to the donors' human colon cancer tissues, the major process was an epithelium-like proliferation process (epithelial duct forming pattern) in the case of well-differentiated adenocarcinoma; the major process was an invasive proliferation process (invasive EMT pattern), while including an epithelium-like proliferation process (epithelial duct forming pattern) in the case of moderately-differentiated adenocarcinoma; and the major process was an invasive proliferation process (invasive EMT pattern) in the case of poorly-differentiated adenocarcinoma.

Figure 5:
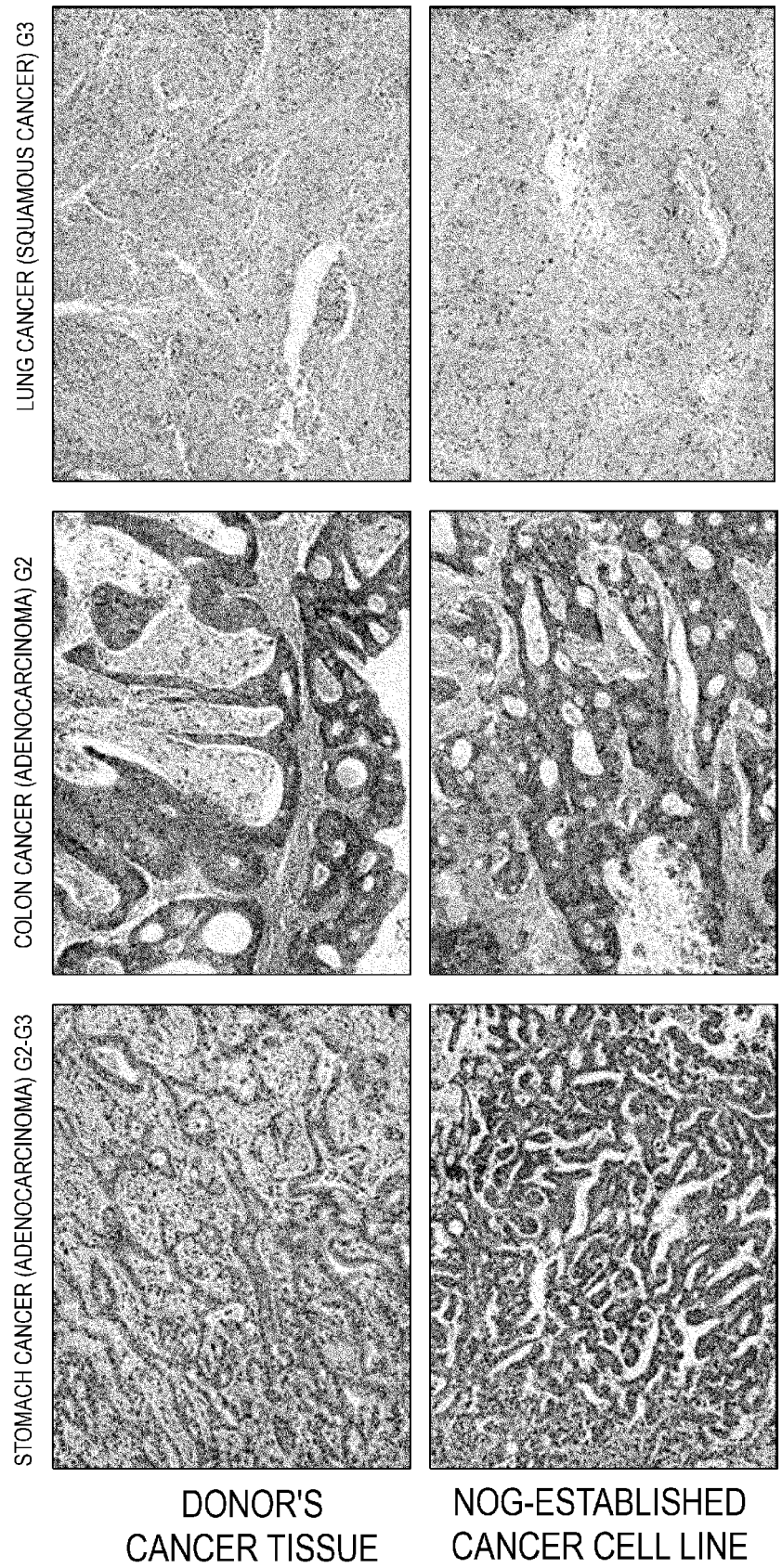
FIG. 5 shows photographs depicting donors' cancer tissues and the reproducibility of the tissue organization by NOG-established cancer cell lines (established by three or more passages). As shown in the photographs, the NOG-established cancer cell lines repeatedly mimic the tissue organization of donors' cancer tissues.

Furthermore, the hierarchical differentiation unique to each line can be repeatedly mimicked even after several transplant passages (FIG. 5).

TABLE 1

Time-dependent changes of the formation of hierarchical organization for each NOG-established line

| | well differentiated | | | | moderate differentiated | | | | poor differentiated | | | |
|---|---|---|---|---|---|---|---|---|---|---|---|---|
| | 3[a] | 7 | 14 | 17 | 3 | 7 | 14 | 21 | 3 | 7 | 14 | 21 |
| Epithelial duct forming pattern | | | | | | | | | | | | |
| Poor differentiated duct | − | + | + | + | − | − | + | + | − | − | − | − |
| Moderate differentiated duct | − | 2+ | 3+ | 3+ | − | − | + | + | − | − | − | − |
| Well differentiated duct | − | − | 2+ | 3+ | − | − | − | − | − | − | − | − |
| Invasive EMTpattern[b] | | | | | | | | | | | | |
| Polygonal cell alignment | − | − | − | − | − | − | − | − | 2+ | + | − | − |
| Duct with invasion front | − | + | + | + | + | + | 2+ | 3+ | − | 2+ | 2+ | 2+ |
| Dissociated cluster | − | + | + | + | − | + | 2+ | 2+ | − | 2+ | 2+ | 2+ |
| Dissociated single cell | − | − | + | + | − | − | 2+ | 2+ | − | − | + | − |

[a]Days after inoculation
[b]β-catenin nuclear accumulation are detected in the IHC sections.

Example 3

Unique Cancer Stem Cells Having the Nature Responsible for the Formation of Each Hierarchical Organization are Detected Among an NOG-Established Cancer Cell Line (1) NOG-Established Cancer Cell Line and Staining Method Cancer stem cells are known to be slow-cycling cells whose cell turnover is in general very slow (Li L, Neaves W B. Cancer res. 2006; 66: 4553-4557). The present inventors focused on this nature and started continuous labeling of BrdU, which is incorporated at the mitotic phase, at the same time when an NOG-established cancer cell line was subcutaneously transplanted into NOG mice. After 14 days of labeling, the mice were dissected to process the tissues. HE staining was performed in the same manner as described above to observe the morphologies of the tissues. In addition, BrdU-incorporated cells were detected by IHC staining (antibody, Beckton Dickinson), and IHC staining was carried out using an antibody against Ki67 (DakoCytomation) as a mitotic phase marker to identify proliferative cells and slow-cycling cells. Moreover, samples adjacent to those described above were stained by IHC using an antibody (MBL) against Lgr5 that is known as a cancer stem cell marker (McDonald S A C, et al., Virchows Arch. (2009) 455: 1-13).

(2) Results and Conclusions

Figure 6:
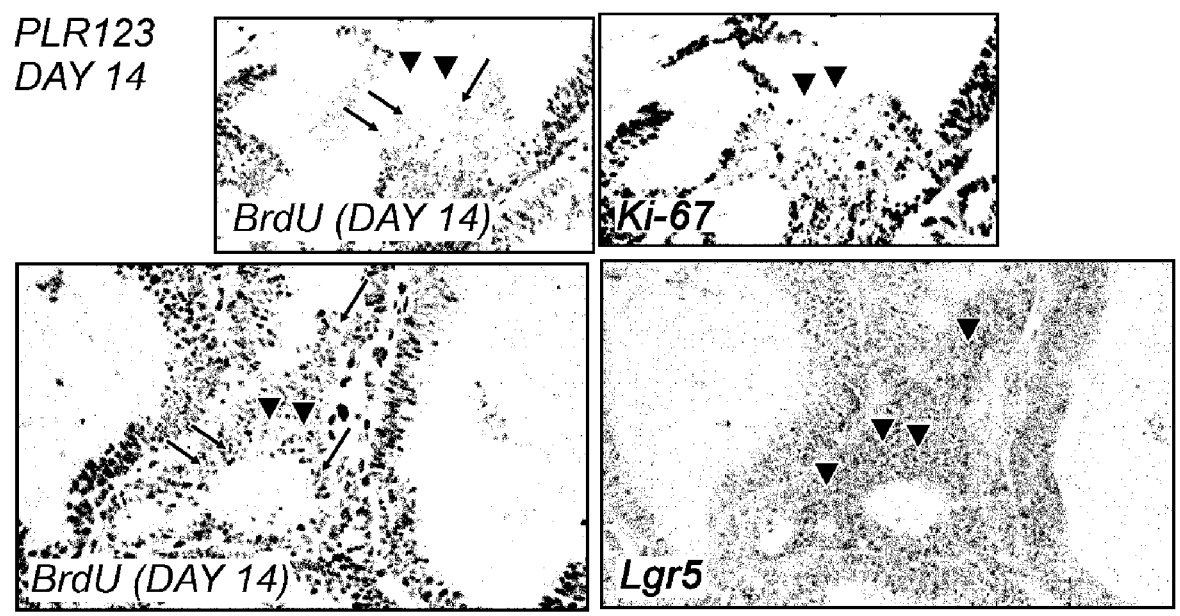
FIG. 6 shows photographs depicting cancer stem cells in an epithelium-like growth area. In the epithelium-like growth area, slow growing cells (slow-cycling cells, closed triangle), which are not labeled by continuous BrdU labeling, are detected among epithelial cells. The cells in the BrdU-negative cell area are positive for a cancer stem cell marker (Lgr5).
Figure 7:
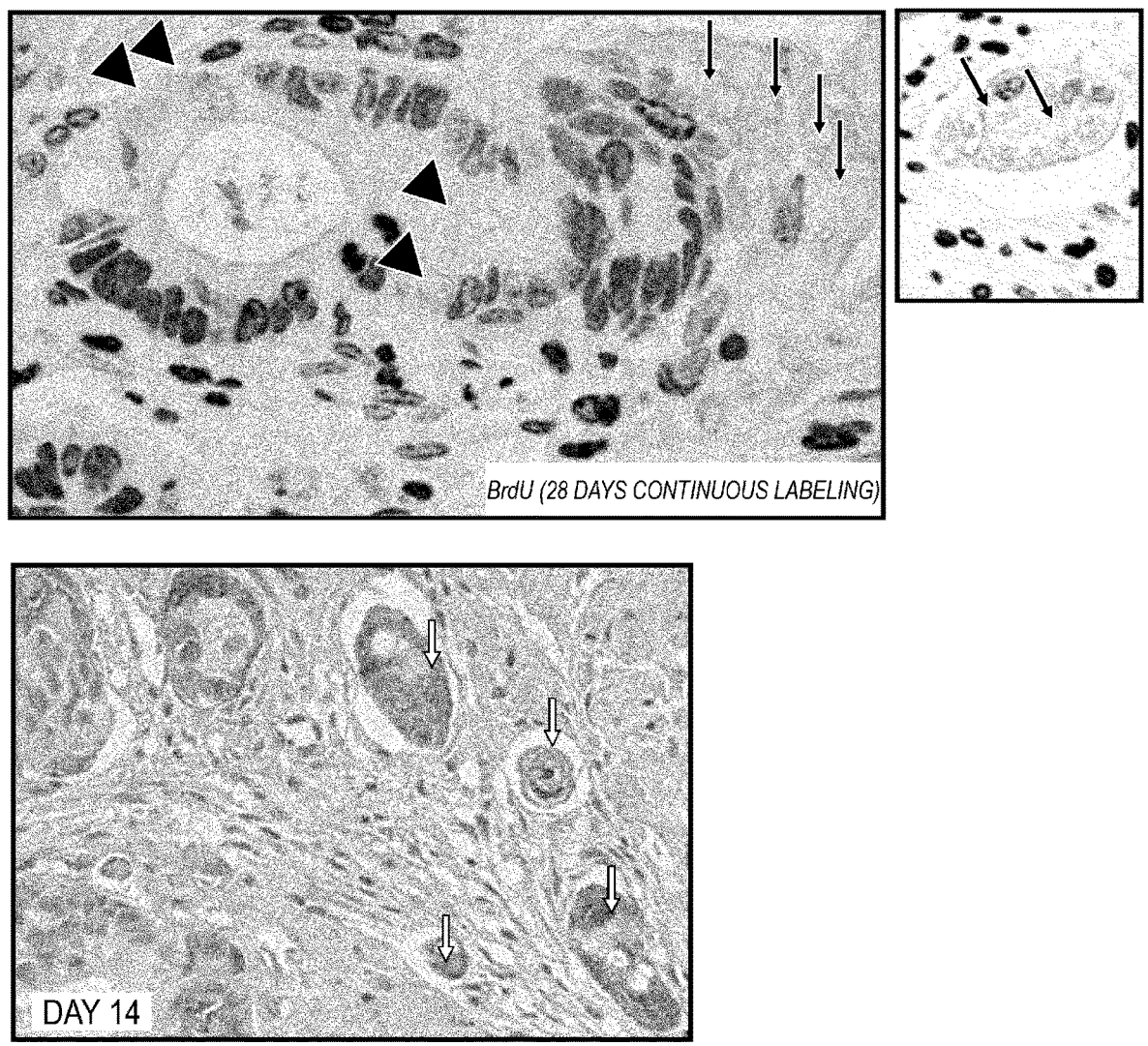
FIG. 7 shows photographs depicting cancer stem cells in the invasive growth area. In the invasive growth area, slow-cycling cells (closed triangle), which are not labeled by continuous BrdU labeling, are detected in the area with epithelial glandular structures. Such slow-cycling cells (closed arrow) are also observed in the invasive area as well as among cells exhibiting the clustering which is assumed to occur in the cellular invasion process. The cells described above are positive for a cancer stem cell marker (Lgr5) (open arrow).
Figure 8:
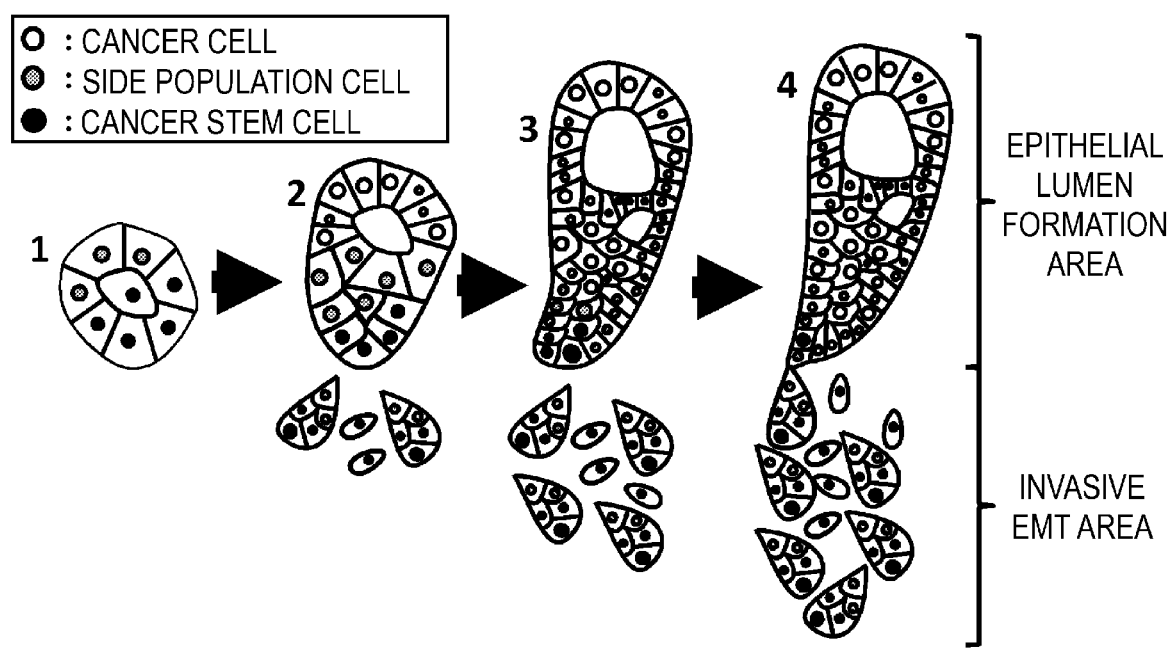
FIG. 8 is a diagram showing the relationship between tumor hierarchical organization and cancer stem cells.

Tissues treated by continuous BrdU labeling showed that both epithelium-like growth area and invasive growth area contained some non-labeled cells. The cells were negative for Ki67. The findings described above suggest that both areas include slow-cycling cells whose cell turnover is very slow, which is known to be a characteristic of cancer stem cells. When samples adjacent to the above samples were stained for Lgr5, which is a cancer stem cell marker, the stained images were consistent with the localization of the slow-cycling cells (FIG. 6). These slow-cycling cells were detected in both epithelium-like growth area and invasive growth area (FIG. 7). Considering the process leading to the formation of the hierarchical organization, which is described in Example 2, the above-described finding suggests that the transition of cancer stem cell localization and the formation of the hierarchical organization can be summarized as shown in FIG. 8.

The existence of stationary stem cells, which are localized in the epithelium-like growth area, and migrating stem cells, which contribute to the formation of hierarchical organization at metastatic sites, has previously been predicted based on observations of human colon cancer. However, the present experiments demonstrated the existence of stem cells described above, as shown in FIG. 8, and also showed that these cells are not two different types of cancer stem cells but they switch to one another, and the transition is involved in the formation of the hierarchical organization in tumor.

In addition, as described in Example 2, the NOG-established cancer cell lines faithfully mimicked the final destination of differentiation in each donor's human cancer tissue. This was always mimicked even after several passages. Thus, it was proven that the cancer stem cells present in the tissues determined the respective final destinations of differentiation. The findings described above show that the models of the present invention are suitable to assess the biological properties unique to cancer stem cells.

Example 4

The Plasticity of Cancer Stem Cells can be Observed by Monitoring them Over Two Generations Using IdU and BrdU (1) NOG-Established Cancer Stem Cell Line and Staining Method Continuous IdU labeling was started at the same time when an NOG-established cancer cell line was subcutaneously transplanted into NOG mice. After 28 days of labeling, the mice were dissected to prepare an IdU-labeled transplanted cell line for the next generation. Continuous BrdU labeling was started at the same time when the cell line was transplanted for the next generation. The mice were dissected three days after transplantation and the tissue treatment was performed. The resulting serial tissue sections were stained by IHC using an antibody recognizing both IdU and BrdU (Beckton Dickinson) and an antibody recognizing BrdU alone (Serotec) in order to detect transitions of proliferative cells and slow-cycling cells over the generations.

(2) Results and Conclusions

Figure 9:
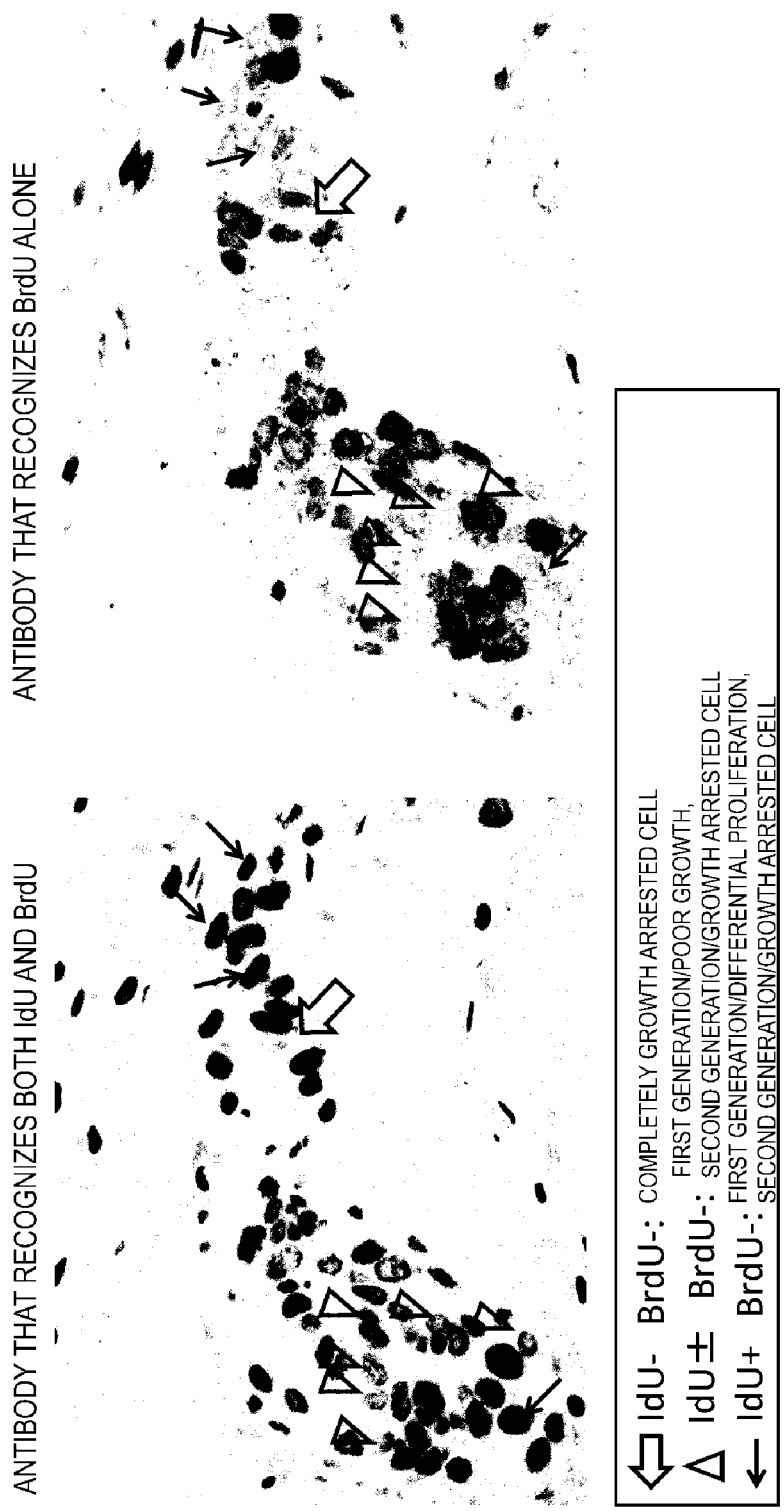
FIG. 9 shows photographs depicting samples in the experiment of continuous IdU/BrdU labeling over two generations. Cells observed are:
cells which remained resting over two generations (open arrow);
cells which grew slowly in the first generation but stopped growing in the second generation (open triangle); and
cells which underwent differential proliferation in the first generation but stopped growing and became stem cells (arrow).

As shown in FIG. 9, when the second-generation samples three days after transplantation were stained by IHC, it is found that cells were positively stained with the antibody recognizing both IdU and BrdU, while some cells were negatively stained with the antibody recognizing BrdU alone. The above staining result demonstrates that the cells took up IdU in the first generation whereas did not take up BrdU in the second generation. This suggests that differentiated cells underwent cell division in the first generation but stopped growing and underwent transition into slow- or non-proliferating cells (stem cells) in the second generation.

The above-described phenomenon that cells which had once undergone differential proliferation undergo transition into stem cells has been regarded as a biological property of cancer stem cells, which is called plasticity (Gupta P B. et al., Nature med. (2009) 15: 1010-12). Thus, the findings described above show that the models of the present invention are suitable to assess the plasticity that is a biological property of cancer stem cells.

Example 5

Cells Expressing P53 Protein at a Low Level, which are Involved in the Reprogramming of Stem Cells, are Found to be Consistent with Cancer Stem Cells (1) NOG-Established Cancer Stem Cell Line and Staining Method Recent years have shown that P53 protein is involved in the transition of somatic cells into stem cells by reprogramming, because, when producing so-called induced pluripotent stem (iPS) cells, the production efficiency is drastically increased by reducing the expression level of the P53 protein. Furthermore, this mechanism has been reported to play an important part in cancer stem cells (Krizhanovsky V and Lowe S W, Nature 2009; 460: 1085-6).

In this context, to test whether cancer stem cells found among an NOG-established cancer cell line are consistent with cells expressing low levels of P53, the present inventors subcutaneously transplanted established cell lines into NOG mice treated by continuous BrdU labeling. The mice were dissected 28 days after transplantation and tissue processing was performed. The resulting serial tissue sections were visualized by IHC staining using an antibody against P53

(DakoCytomation) and an antibody against BrdU (Beckton Dickinson). The sections were observed to assess the consistency.

(2) Results and Conclusions

Figure 10:
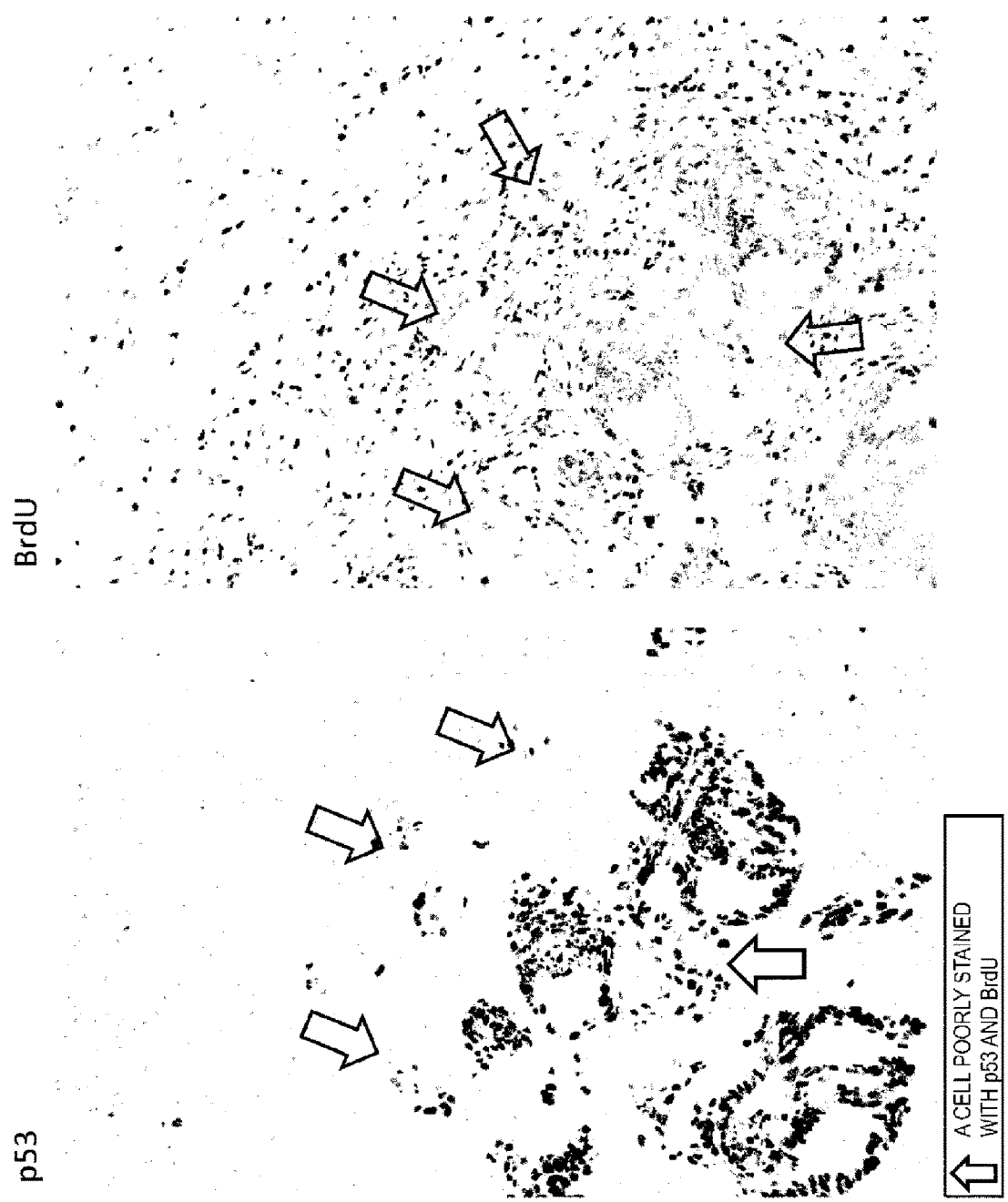
FIG. 10 shows photographs depicting samples immunostained with anti-P53 antibody and anti-BrdU antibody. Cells weakly positive or negative for P53 and BrdU (open arrow) are detected.

P53 has been reported to be overexpressed in many cancers (Toledo F and Wahl G M., Nature rev cancer (2006) δ: 909-923). The present invention also revealed that the protein was overexpressed in many NOG-established cancer cells. Meanwhile, loss or reduced expression of P53 was consistent with BrdU-negative or weakly positive cells (FIG. 10).

In recent years, as a biological property of stem cells including cancer stem cells, the reduced expression of P53 protein has been demonstrated to play an important role in so-called reprogramming which results in acquisition of pluripotency by somatic cells. Accordingly, the finding that the expression level of P53 protein is also reduced in the cancer stem cells of the models of the present invention suggests that a reprogramming mechanism similar to stem cells works in these cancer stem cells. Thus, the models of the present invention were demonstrated to be suitable to assess their biological properties.

Example 6

The Process Leading to Transition of Cancer Cells into Tumor Stroma-Forming Fibroblasts Through Complete-EMT can be Observed with NOG-Established Cancer Cell Lines (1) NOG-Established Cancer Cell Line and Staining Method NOG-established cancer cell lines were subcutaneously transplanted into NOG mice. The animals were dissected 14 days after transplantation to obtain tumor masses. By IHC staining specific to human β2 microglobulin, the tumor masses were assessed for species origin.

In addition, before in vitro culture, cells to be plated were tested for the species origin by flow cytometry using Anti-Human HLA-ABC Antigen/RPE antibody (DAKO, Cat. No. R7000; human specific) and Anti-mouse MHC class I antibody (Abcam, Cat. No. ab15680-50; mouse specific). Then, the cells were cultured in Medium 1 to monitor the emergence of fibroblast-like cells.

(2) Results and Conclusions

Figure 11:
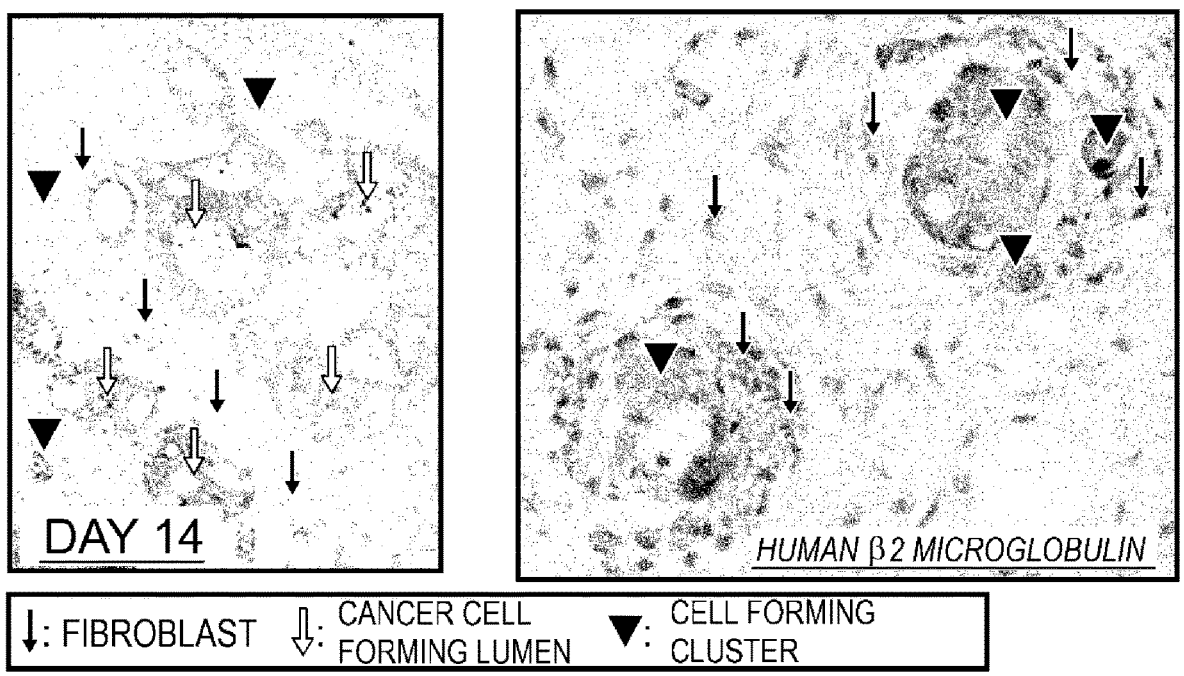
FIG. 11 shows photographs depicting human-derived fibroblasts.

Human-derived fibroblasts were observed in the tumor stroma (FIG. 11).

Figure 12:
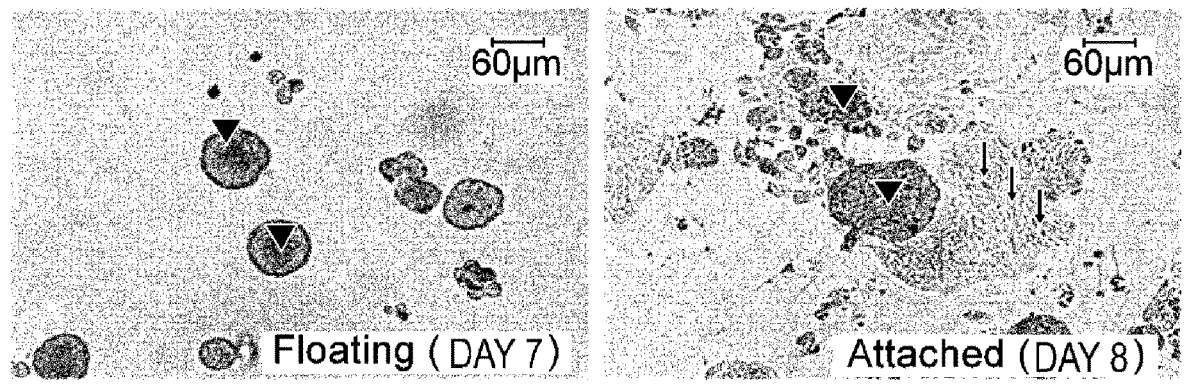
FIG. 12 shows photographs and diagrams depicting in vitro growth of human-derived fibroblasts. Only epithelium-like cells (closed triangle) were observed but fibroblasts were undetectable under the suspension culture conditions. Meanwhile, when the cells are adhered, fibroblast-like cells (closed arrow) grew. Furthermore, using an anti-human MHC antibody, 90% of the cells were confirmed to be human-derived cells.
Figure 12:
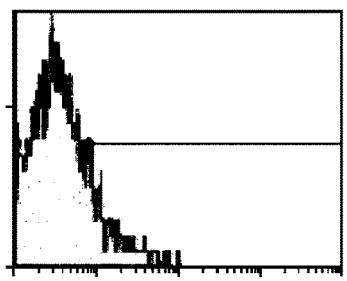
Figure 12:
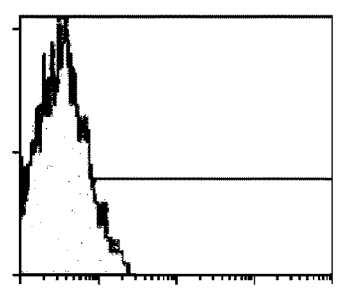
Figure 12:
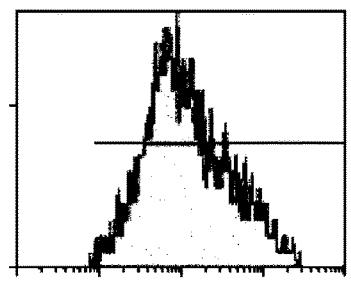
Figure 12:
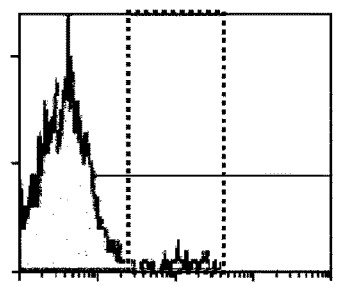

Furthermore, cells which had been confirmed to include about 90% of human cells before culture were cultured in Medium 1 used in Example 1. The emergence of fibroblasts was detected (FIG. 12).

Example 7

The Models of the Present Invention Enable Detection of Morphological Structures Characteristic of Resistance to Anti-Cancer Agents (1) Detection of NOG-Established Cancer Cell Line-Derived Cells Resistant to Anti-Cancer Agents Well-differentiated adenocarcinoma and moderately-differentiated adenocarcinoma were each transplanted into three heads of NOG mice, and 5-fluorouracil (5-FU, Mayne Pharma) was administered at 100 mg/kg into the peritoneal cavities 7, 10, and 14 days after transplantation, a total of three times. On the day following the final administration (15 days after transplantation), the tumor masses were harvested and processed by the same method as described above to prepare HE-stained samples. The samples were histopathologically compared with samples prepared from a control group (3 cases) administered with the vehicle alone.

(2) Results and Conclusions

Figure 13:
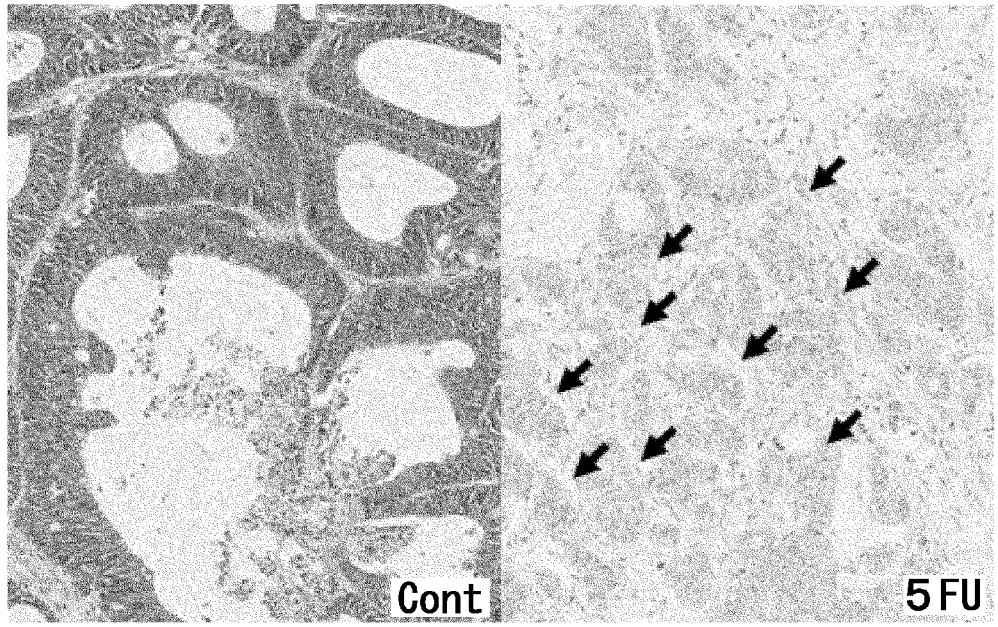
FIG. 13 shows photographs depicting the histopathology of cancer cells resistant to anti-cancer agents, which were observed after administration of an anti-cancer agent (5-fluorouracil) to NOG mice transplanted with an NOG-established colon cancer cell line. These photographs indicate an increase of poorly-differentiated glandular ducts (closed arrow) and a decrease of budding structures (broken line).
Figure 13:
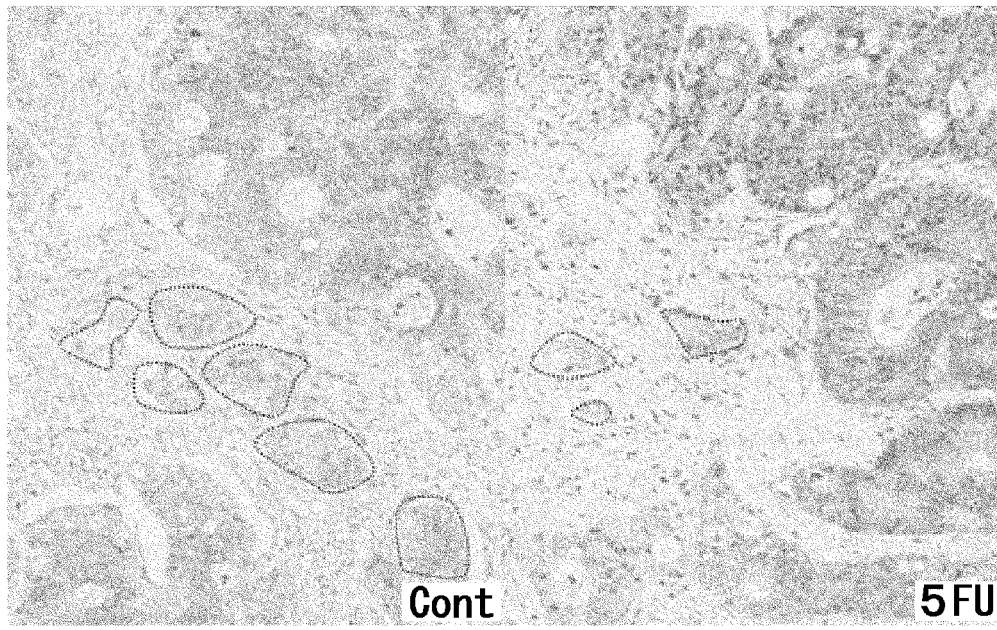

As shown in Table 2 and FIG. 13, with respect to well-differentiated adenocarcinoma, the highly differentiated glandular structure was reduced and poorly differentiated glandular ducts with an unclear glandular structure were dominantly observed as compared to the control group. As for moderately-differentiated adenocarcinoma, the budding was reduced, whereas poorly differentiated glandular ducts were observed as the major histological structure. The findings described above demonstrate that sites sensitive to anti-cancer agents are: (1) the glandular structural sites formed via the epithelium-like growth process with active proliferation in well-differentiated adenocarcinoma and (2) the budding structural sites during the process of invasive proliferation in moderately-differentiated adenocarcinoma. Meanwhile, poorly differentiated glandular ducts were shown to be resistant to anti-cancer agents.

As described above, since characteristic groups of cells and tissue structures that were resistant to anti-cancer agents were observed, the models of the present invention are expected to be applicable to assess processes of selecting anti-cancer agents, processes of acquiring the resistance as a result of a long-term drug treatment, processes of recurrence after treatment with anti-cancer agents, etc. Thus, the present invention demonstrated that the models of the present invention enables search for factors involved in the above-described processes and search/screening for pharmaceutical agents that target an above-described factor.

TABLE 2

CHARACTERISTIC STRUCTURES OBSERVED WITH EACH LINE AFTER 5-FU ADMINISTRATION

| | Well differentiated | | | | | | Moderate differentiated | | | | | |
| --- | --- | --- | --- | --- | --- | --- | --- | --- | --- | --- | --- | --- |
| | C1[a] | C2 | C3 | F1 | F2 | F3 | C1 | C2 | C3 | F1 | F2 | F3 |
| Epithelial duct forming pattern | | | | | | | | | | | | |
| Poor differentiated duct | + | + | + | 2+ | 3+ | 2+ | + | + | + | + | + | + |
| Moderate differentiated duct | 3+ | 3+ | 3+ | 3+ | + | + | + | + | + | + | + | + |
| Well differentiated duct | 2+ | 2+ | 2+ | + | + | 2+ | − | − | − | − | − | − |
| Invasive EMT pattern | | | | | | | | | | | | |
| Dissociated cluster | ± | ± | ± | ± | ± | ± | 2+ | 2+ | 2+ | + | + | + |

[a]C, Control; F, 5FU administration

INDUSTRIAL APPLICABILITY

The present invention's non-human animal models and culture systems with NOG-established cancer cell lines can be considered as models that reflect more closely the pathology of human cancer patients, because they maintain the hierarchical organization of cancer cells unique to human cancer patients, exhibit the cancer progression process, and faithfully mimic the biological properties thereof. Thus, the present invention's non-human animal models and culture systems with NOG-established cancer cell lines can be effectively used to screen for agents that produce a preventive or therapeutic effect against human cancer or to assess the drug efficacy of the agents. Accordingly, the present invention can contribute to the development of pharmaceutical agents for preventing or treating human cancer.

What is claimed is:

1. A method of searching for an anti-cancer agent target, which comprises the steps of:
    (1) preparing a mouse model of human colon cancer by transplanting an NOD/SCID/gamma(c)(null) NOG-established colon cancer cell line into a mouse,
    wherein the NOD/SCID/gamma(c)(null) (NOG)-established cancer cell line was established by transplanting a human colon cancer tissue into a severely immunodeficient NOG mouse, and
    wherein the mouse model of human colon cancer comprises:
        (a) cancer stem cells in an epithelium-like glandular area, and in an invasive area, detected using continuous BrdU labelling, Ki67 staining, or Lgr5 staining, and
        (b) partial epithelial-mesenchymal transition (EMT) cells derived from cancer stem cells in the invasive area, detected by a lack of E-cadherin expression at a contact surface of a tumor cell with stroma cells or presence of fibronectin expression,
    (2) identifying a tissue piece from the mouse model of human colon cancer comprising fibroblasts derived from human colon cancer cells through complete epithelial-mesenchymal transition (complete-EMT) in a tumor stroma using IHC staining,
    (3) collecting the tissue piece identified in step (2);
    (4) assessing the expression of DNA, RNA, or protein in the collected tissue piece of (3); and
    (5) identifying DNA, RNA, or protein that changes in a manner dependent of hierarchical organization and cancer progression process of a cancer cell in the tissue piece, thereby identifying the anti-cancer agent target,
    wherein the hierarchical organization comprises a two-layer structure comprising an epithelium-like glandular structure and an invasive area, and
    wherein the cancer progression process comprises:
        (a) an epithelial duct-forming pattern or
        (b) an invasive EMT pattern, while including an epithelial duct-forming pattern.

2. The method of claim 1, further comprising in step (2) detecting morphologies comprising budding, clustering tumor cells, dissociated single tumor cells, or reconstruction of tubules in the invasive area.

3. A method of searching for an anti-cancer agent target, which comprises the steps of:
    (1) preparing a mouse model of human colon cancer by subcutaneously transplanting an NOD/SCID/gamma(c)(null) (NOG)-established colon cancer cell line into a mouse,
    wherein the NOD/SCID/gamma(c)(null) (NOG)-established cancer cell line was established by transplanting a human colon cancer tissue into a severely immunodeficient NOG mouse, and
    wherein the mouse model of human colon cancer comprises:
        (a) cancer stem cells in an epithelium-like glandular area, and in an invasive area, detected using continuous BrdU labelling, Ki67 staining, or Lgr5 staining, and
        (b) partial epithelial-mesenchymal transition (EMT) cells derived from cancer stem cells in the invasive area, detected by a lack of E-cadherin expression at a contact surface of a tumor cell with stroma cells or presence of fibronectin expression,
    (2) identifying a tissue piece from the mouse model of human colon cancer comprising fibroblasts derived from human colon cancer cells through complete epithelial-mesenchymal transition (complete-EMT) in a tumor stroma using IHC staining
    (3) collecting the tissue piece identified in step (2);
    (4) assessing the expression of DNA, RNA, or protein in the collected tissue piece of (3); and
    (5) identifying DNA, RNA, or protein that changes in a manner dependent of hierarchical organization and cancer progression process of a cancer cell in the tissue piece, thereby identifying the anti-cancer agent target,
    wherein the hierarchical organization comprises a two-layer structure comprising an epithelium-like glandular structure and an invasive area, and
    wherein the cancer progression process comprises:
        (a) an epithelial duct-forming pattern or
        (b) an invasive EMT pattern, while including an epithelial duct-forming pattern.

4. The method of claim 3, further comprising in step (2) detecting morphologies comprising budding, clustering tumor cells, dissociated single tumor cells, or reconstruction of tubules in the invasive area.

5. The method of claim 1, further comprising in step (2) detecting cancer stem cells with continuous BrdU labelling, Ki67 staining, and Lgr5 staining.

6. The method of claim 3, further comprising in step (2) detecting cancer stem cells with continuous BrdU labelling, Ki67 staining, and Lgr5 staining.

* * * * *